(12) United States Patent
Yamamoto

(10) Patent No.: US 7,916,298 B2
(45) Date of Patent: Mar. 29, 2011

(54) ANALYZER AND ANALYTIC SYSTEM

(75) Inventor: Norimasa Yamamoto, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 12/655,734

(22) Filed: Dec. 14, 2009

(65) Prior Publication Data
US 2010/0110415 A1 May 6, 2010

Related U.S. Application Data

(63) Continuation of application No. 11/477,281, filed on Jun. 29, 2006, now abandoned.

(30) Foreign Application Priority Data

Jul. 1, 2005 (JP) .................................. 2005-193955

(51) Int. Cl.
*G01N 21/00* (2006.01)

(52) U.S. Cl. .......................... 356/432; 356/244; 356/440

(58) Field of Classification Search .......... 356/244–246, 356/432, 440–442

See application file for complete search history.

(56) References Cited

U.S. PATENT DOCUMENTS

| | | | |
|---|---|---|---|
| 5,283,178 A | | 2/1994 | Kessler et al. |
| 5,825,478 A | * | 10/1998 | Wilcox et al. ................... 356/73 |
| 6,373,074 B1 | * | 4/2002 | Mueller et al. ................ 250/584 |
| 6,608,671 B2 | * | 8/2003 | Tsien et al. ...................... 356/72 |
| 2005/0106745 A1 | | 5/2005 | Wexler et al. |

FOREIGN PATENT DOCUMENTS

| | | |
|---|---|---|
| JP | 61-029740 A | 2/1986 |
| JP | 61-088158 A | 5/1986 |
| JP | 02-284064 | 11/1990 |
| JP | 08-315783 A | 11/1996 |
| JP | 10-170432 | 6/1998 |

* cited by examiner

*Primary Examiner* — Tarifur Chowdhury
*Assistant Examiner* — Tara S Pajoohi
(74) *Attorney, Agent, or Firm* — Brinks Hofer Gilson & Lione

(57) ABSTRACT

This analyzer comprises a photoirradiation portion simultaneously photoirradiating a plurality of storage vessels storing a plurality of measurement samples respectively and a plurality of photodetection portions detecting a plurality of light components resulting from simultaneous photoirradiation on the plurality of storage vessels storing the plurality of measurement samples respectively. The photoirradiation portion includes a light source, a first light guide portion branching light emitted from the light source into a plurality of light components and guiding the plurality of light components to the plurality of measurement samples respectively and a second light guide portion branching light emitted from the light source into a plurality of light components and guiding the plurality of light components to the plurality of measurement samples respectively.

12 Claims, 19 Drawing Sheets

CALCULATION OF n WITH CONTROL PORTION

| 48 μsec STEP | CH (MUX NUMBER) | | |
|---|---|---|---|
| | LINE L0 | LINE L1 | LINE L2 |
| 0 | CH0 (0) | CH16 (0) | CH32 (0) |
| 1 | CH0 (0) | CH16 (0) | CH32 (0) |
| 2 | CH0 (0) | CH16 (0) | CH32 (0) |
| 3 | CH1 (1) | CH16 (0) | CH32 (0) |
| 4 | CH1 (1) | CH17 (1) | CH32 (0) |
| 5 | CH1 (1) | CH17 (1) | CH33 (1) |
| 6 | CH2 (2) | CH17 (1) | CH33 (1) |
| 7 | CH2 (2) | CH18 (2) | CH33 (1) |
| ⋮ | ⋮ | ⋮ | ⋮ |
| 44 | CH14 (14) | CH30 (14) | CH46 (14) |
| 45 | CH15 (15) | CH30 (14) | CH46 (14) |
| 46 | CH15 (15) | CH31 (15) | CH46 (14) |
| 47 | CH15 (15) | CH31 (15) | CH47 (15) |
| 48 | CH0 (0) | CH31 (15) | CH47 (15) |
| 49 | CH0 (0) | CH16 (0) | CH47 (15) |
| 50 | CH0 (0) | CH16 (0) | CH32 (0) |

▨ MULTIPLEXER SWITCHING + NORMALIZATION + AMPLIFICATION
☐ SIGNAL WAIT PROCESSING
▰ A-D CONVERSION + DATA STORAGE

ANALYZER AND ANALYTIC SYSTEM

This application is a continuation of prior application Ser. No. 11/477,281, filed Jun. 29, 2006, which claims priority under 35 U.S.C. §119 to Japanese Patent Application No. JP2005-193955 filed Jul. 1, 2005, the entire contents of both of which are hereby incorporated by reference.

BACKGROUND

Field of the Invention

The present invention relates to an analyzer and an analytic system.

In biochemical analysis or blood coagulation analysis, an analyzer applies light to a sample for obtaining the quantity of transmitted light or absorbance, and analyzes the sample on the basis of this optical information. An analyzer of this type must optically measure a large number of samples at the same time. An analyzer disclosed in Japanese Patent Laying-Open No. 2-284064 (1990) applies light emitted from a single light source to the overall incidence end of an optical fiber bundle, thereby introducing the light emitted from the light source into the optical fiber bundle. This optical fiber bundle has a plurality of branched exit ends, for applying light components to a plurality of reaction vessels from the exit ends respectively. Thus, this analyzer can optically measure a plurality of samples at the same time.

In order to improve the throughput of an analyzer, the number of samples optically measurable at the same time must be increased. When the analyzer branches light with a single optical fiber bundle as in the analyzer disclosed in the aforementioned Japanese Patent Laying-Open No. 2-284064, however, the area of the incidence end of the optical fiber bundle is increased as the number of branching is increased, to reduce the quantities of light components outgoing from the exit ends. Further, the surface of the incidence end of the optical fiber bundle is so planar that the quantities of light components transmitted through respective optical fiber members are dispersed unless the analyzer uniformly applies light to the surface of the incidence end.

On the other hand, an analyzer disclosed in Japanese Patent Laying-Open No. 10-170432 (1998) is so formed as to supply light emitted from a single light source portion (photoirradiator) to a plurality of terminal portions while applying the supplied light to samples set on the terminal portions respectively. The light applied to the samples is incident upon a single array-type photoreceptor provided in common to the respective terminal portions. Therefore, the conventional analyzer disclosed in the aforementioned Japanese Patent Laying-Open No. 10-170432, supplying light to the terminal portions from the single light source portion, can be downsized.

However, the downsizeable conventional analyzer disclosed in the aforementioned Japanese Patent Laying-Open No. 10-170432, which is so formed as to detect light with the single array type photoreceptor, cannot simultaneously introduce light components from the terminal portions into the array type photoreceptor for performing measurement. Therefore, the conventional analyzer disclosed in the aforementioned Japanese Patent Laying-Open No. 10-170432 must introduce the light components from the terminal portions into the array-type photoreceptor with a time lag, to disadvantageously require a long time for measurement in the respective terminal portions.

SUMMARY OF THE INVENTION

An object of the present invention is to provide an analyzer and an analytic system improved in specimen treatment efficiency while attaining downsizing of the analyzer.

In order to attain the aforementioned object, an analyzer according to a first aspect of the present invention comprises a plurality of detection areas in which containers including the samples are receivable, at least one optical source configured to emit at least one series of lights, and more than one splitter configured to split the at least one series of lights into a plurality of series of lights each guided to one of the plurality of the detection areas at which the sample is optically analyzed.

An analyzer according to a second aspect of the present invention comprises a photoirradiation portion simultaneously photoirradiating a plurality of storage vessels storing a plurality of measurement samples prepared by admixing a reagent with a plurality of samples respectively, a plurality of photodetection portions detecting a plurality of light components resulting from simultaneous photoirradiation on the plurality of storage vessels storing the plurality of measurement samples respectively and an analytic portion analyzing characteristics of the plurality of samples on the basis of the light components detected by the photodetection portions. The photoirradiation portion includes a light source, a first light guide portion branching light emitted from the light source into a plurality of light components and guiding the plurality of light components to the plurality of measurement samples respectively and a second light guide portion branching light emitted from the light source into a plurality of light components and guiding the plurality of light components to the plurality of measurement samples respectively.

An analyzer according to a third aspect of the present invention comprises a photoirradiation portion simultaneously photoirradiating a plurality of storage vessels storing a plurality of measurement samples prepared by admixing a reagent with a plurality of samples respectively, a plurality of photodetection portions detecting a plurality of light components resulting from simultaneous photoirradiation on the plurality of storage vessels storing the plurality of measurement samples respectively and an analytic portion analyzing characteristics of the plurality of samples on the basis of the light components detected by the photodetection portions. The photoirradiation portion includes a light source having a platelike filament and an optical fiber bundle including an incidence end formed by bundling ends of a plurality of optical fibers and a plurality of exit ends directed toward the plurality of storage vessels respectively so that light emitted from a first surface of the platelike filament is incident upon the incidence end.

An analytic system according to a fourth aspect of the present invention comprises a photoirradiator, a first analyzer including a first reagent mixing portion mixing a reagent into an analyte and a first photodetection portion detecting light obtained by applying light emitted from the photoirradiator to the analyte mixed with the reagent by the first reagent mixing portion, a second analyzer including a second reagent mixing portion mixing another reagent into another analyte and a second photodetection portion detecting light obtained by applying light emitted from the photoirradiator to the analyte mixed with the reagent by the second reagent mixing portion and analytic means analyzing characteristics of the analyte mixed with the reagent by the first reagent mixing portion on the basis of the light detected by the first photodetection portion while analyzing characteristics of the analyte mixed with the reagent by the second reagent mixing portion on the basis of the light detected by the second photodetection portion.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENTS

An embodiment of the present invention is now described with reference to the drawings.

The structure of an analytic system 1 according to the embodiment of the present invention is described with reference to FIGS. 1 to 12.

The analytic system 1 according to the embodiment of the present invention is a system for optically measuring and analyzing the quantities and the degrees of activity of specific substances related to a blood coagulative/fibrinolytic function, employing blood plasma as a specimen. The analytic system 1 according to this embodiment optically measures the specimen with a coagulation time method. The coagulation time method employed in this embodiment is a measuring method detecting the process of coagulation of the specimen as change of transmitted light.

Figure 25:
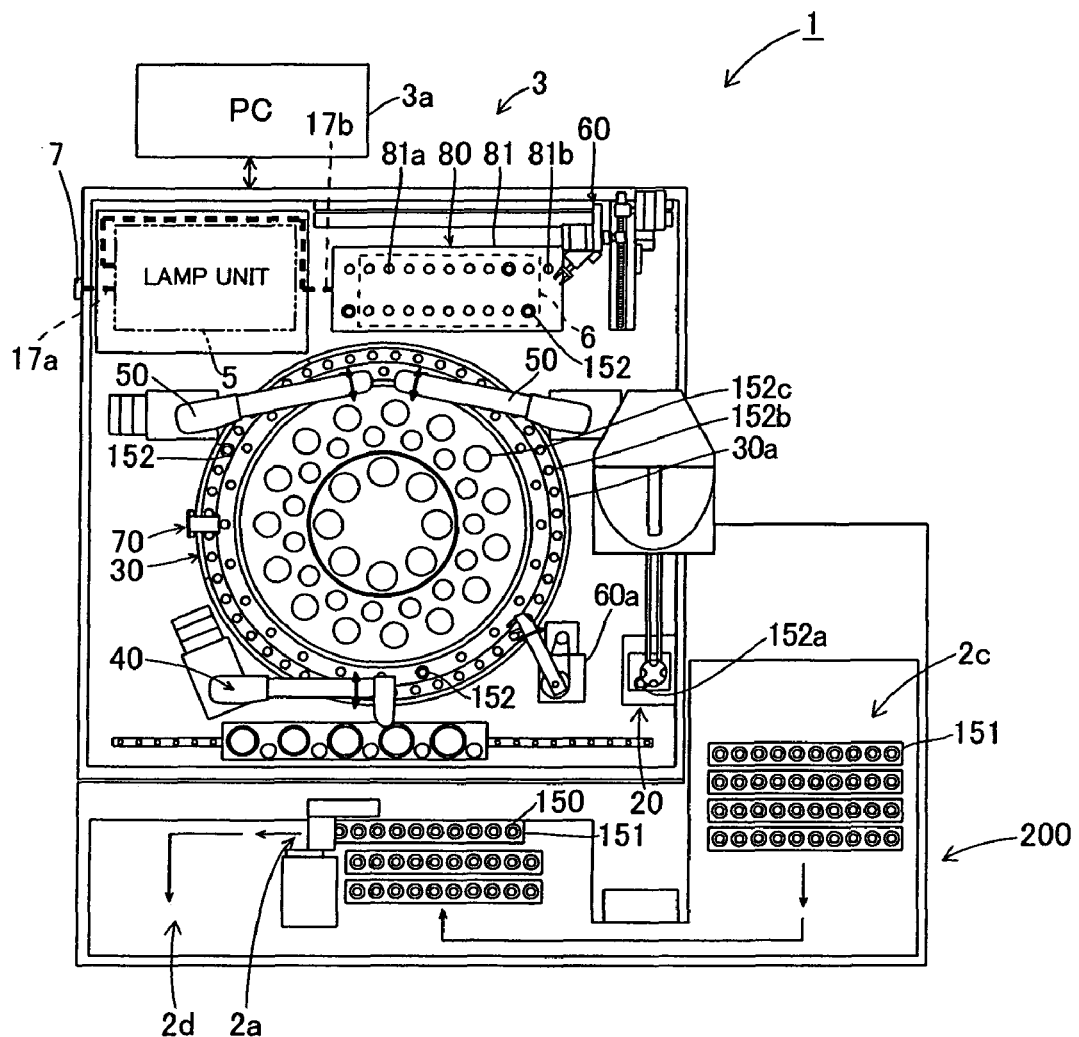
FIG. 25 is a plan view showing the overall structure of the analytic system including no extension analyzer according to the embodiment of the present invention.

The structure of the analytic system 1 can be varied with the scale of an institution where the system 1 is installed. When installed in an institution having a relatively small number of specimens, for example, the analytic system 1 is constituted of an analyzer 3 and a transporter 200 for supplying specimens to the analyzer 3, as shown in FIG. 25. When installed in an institution having a large number of specimens, on the other hand, the analytic system 1 is constituted of a transport mechanism portion 2 substituting for the transporter 200, an analyzer 3 and an extension analyzer 4. The extension analyzer 4 added to the analytic system 1 extends the specimen throughput of the analytic system 1.

Figure 1:
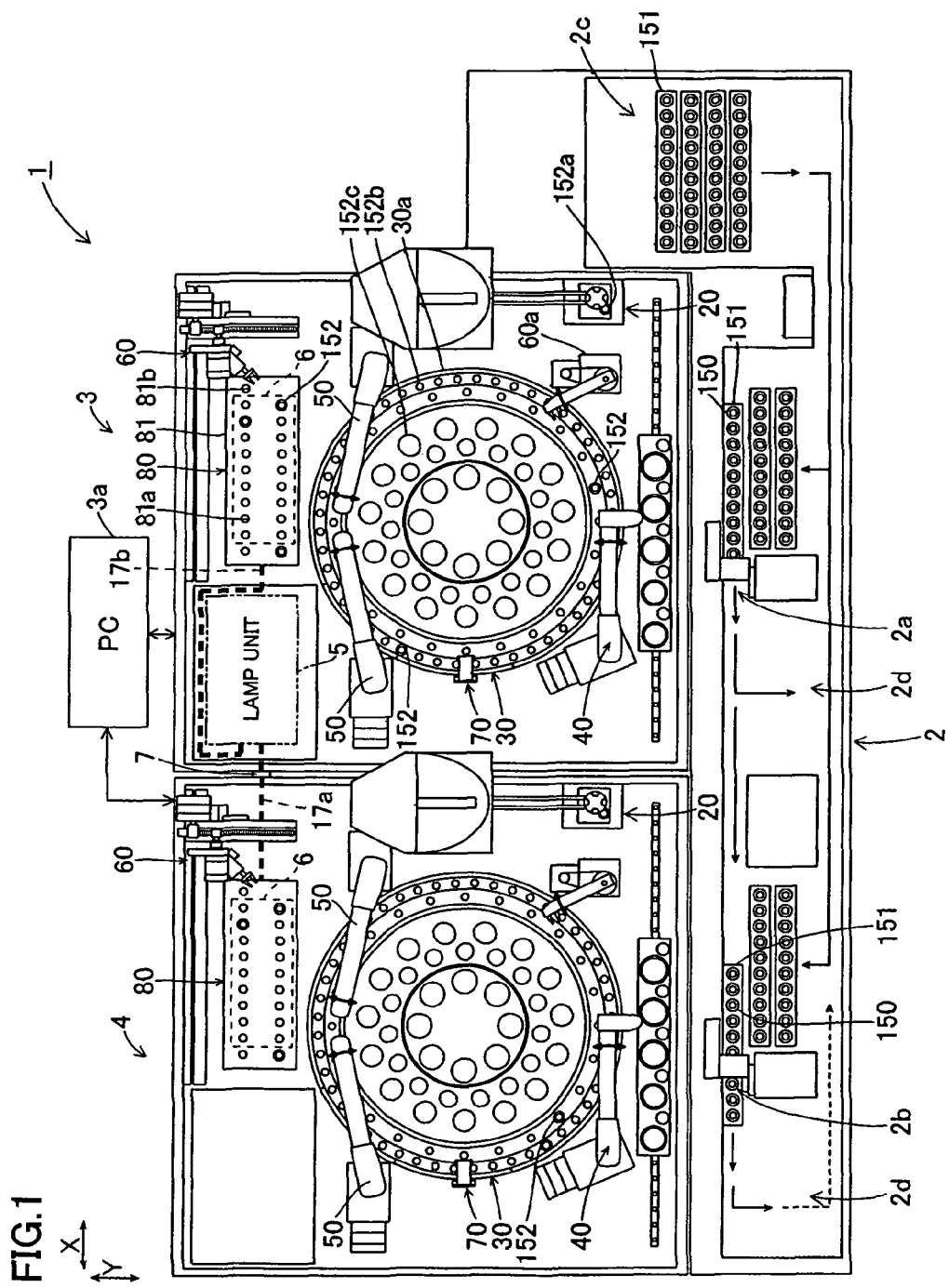
FIG. 1 is a plan view showing the overall structure of an analytic system including an analyzer and an extension analyzer according to an embodiment of the present invention.

The transport mechanism portion 2 shown in FIG. 1 has a function of transporting racks 151 each carrying a plurality of (10 in this embodiment) test tubes 150 storing specimens to suctional positions 2a and 2b (see FIG. 1) of the analyzer 3 and the extension analyzer 4 respectively, in order to supply the specimens to the analyzer 3 and the extension analyzer 4. This transport mechanism portion 2 has a rack set area 2c for setting racks 151 carrying test tubes 150 storing untreated specimens and a rack storage area 2d for storing racks 151 carrying test tubes 150 storing treated specimens.

The analyzer 3 and the extension analyzer 4 are so formed as to optically measure different specimens supplied from the transport mechanism portion 2 thereby acquiring optical information related to the supplied specimens respectively. According to this embodiment, the analyzer 3 and the extension analyzer 4 optically measure specimens injected into cuvettes 152 (see FIG. 1) from the test tubes 150 located on the transport mechanism portion 2 respectively. The analyzer 3 includes an information processing terminal 3a, a lamp unit 5 and a control board 6. The analyzer 3 further includes a cuvette supply portion 20, a rotary transport portion 30, a specimen injection arm 40, two reagent injection arms 50, cuvette transfer portions 60 and 60a, a first optical information acquisitive portion 70 and a second optical information acquisitive portion 80. The extension analyzer 4 also includes a control board 6, a cuvette supply portion 20, a rotary transport portion 30, a specimen injection arm 40, two reagent injection arms 50, cuvette transfer portions 60 and 60a, a first optical information acquisitive portion 70 and a second optical information acquisitive portion 80 identical to those provided on the analyzer 3. These components are identically arranged in the analyzer 3 and the extension analyzer 4.

According to this embodiment, only the analyzer 3 includes the information processing terminal 3a and the lamp unit 5, while the extension analyzer 4 includes no such components.

Figure 2:
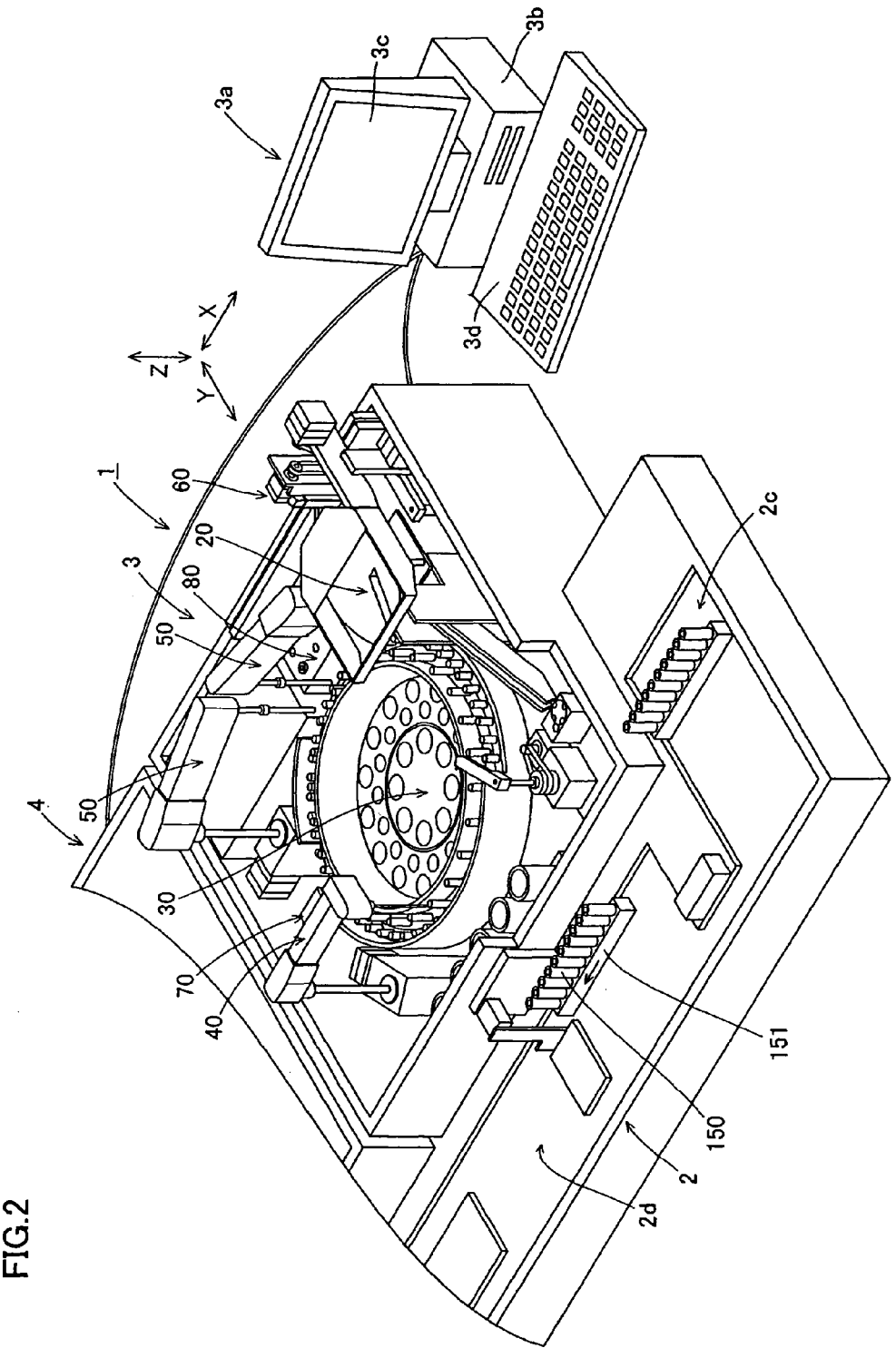
FIG. 2 is a perspective view partially showing the analytic system including the analyzer and the extension analyzer according to the embodiment shown in FIG. 1.

The information processing terminal 3a is electrically connected not only to the body of the analyzer 3 but also to the extension analyzer 4 through communication cables. In other words, the analyzer 3 and the extension analyzer 4 share the information processing terminal 3a of the analyzer 3 in common. The analyzer 3 and the extension analyzer 4 have functions of transmitting optical information acquired from specimens to the information processing terminal 3a. The information processing terminal 3a is formed by a personal computer (PC), and includes a PC body 3b, a display portion 3c and a keyboard 3d, as shown in FIG. 2. When the lamp unit 5 applies light components having prescribed wavelength characteristics to specimens (measurement samples), the PC body 3b analyzes the characteristics of the specimens on the basis of signals (optical information) acquired by signal processing portions 111 and control portions 112, described later, of the control boards 6. According to this embodiment, the PC body 3b of the information processing terminal 3a is so formed as to analyze times (coagulation times) required for the specimens to reach prescribed coagulation states from prescribed timing after reagents are mixed into the specimens. The PC body 3b includes a control portion (not shown) formed by a CPU, a ROM, a RAM, a hard disk etc. The display portion 3c is provided for displaying information such as results of analysis obtained in the PC body 3b. As hereinabove described, the analyzer 3 and the extension analyzer 4 are identical in structure to each other except that the extension analyzer 4 includes neither information processing terminal 3a nor lamp unit 5. Therefore, the structure of the analyzer 3 is described in the following.

Figure 3:
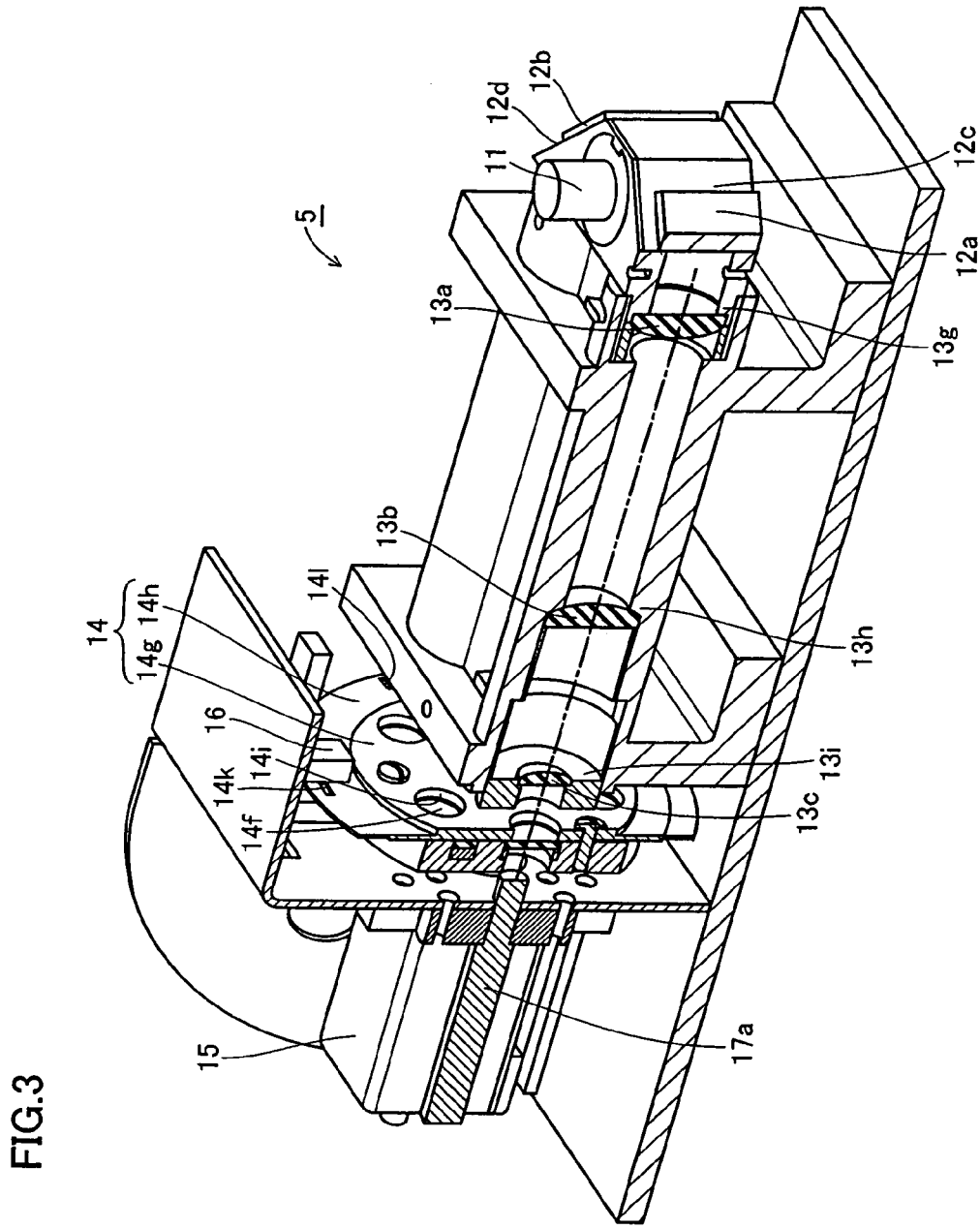
FIG. 3 is a perspective view for illustrating the structure of a lamp unit included in the analyzer according to the embodiment shown in FIG. 1.
Figure 4:
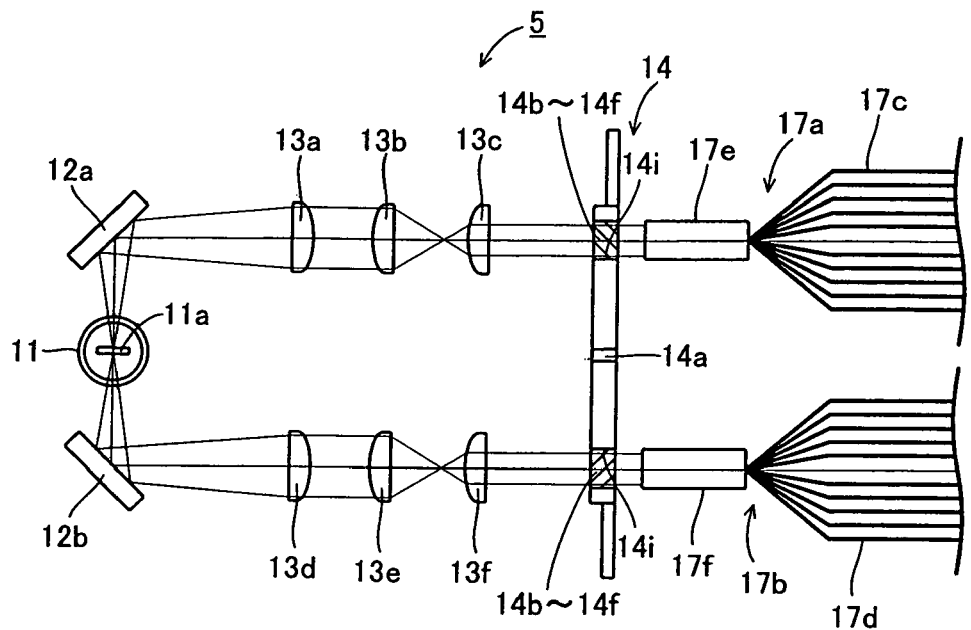
FIG. 4 is a schematic diagram showing the structure of the lamp unit included in the analyzer according to the embodiment shown in FIG. 3.

As shown in FIGS. 3 and 4, the lamp unit 5 has a halogen lamp 11 serving as a light source, two mirrors 12a and 12b, two sets of condensing lenses 13a to 13c and 13d to 13f, a discoidal filter portion 14, a motor 15, a light transmission sensor 16 and two optical fiber members 17a and 17b. In this lamp unit 5, the halogen lamp 11, the mirror 12b, the condensing lenses 13d to 13f and the optical fiber member 17b constitute an optical system for the analyzer 3, while the halogen lamp 11, the mirror 12a, the condensing lenses 13a to 13c and the optical fiber member 17a constitute an optical system for the extension analyzer 4.

The forward end of the optical fiber member 17b is connected to the second optical information acquisitive portion 80 of the analyzer 3. The forward end of the optical fiber member 17a is connected to the second optical information acquisitive portion 80 of the extension analyzer 4 only when the extension analyzer 4 is provided on the analytic system 1.

The mirror 12a, the condensing lenses 13a to 13c and the optical fiber member 17a may not be provided on the lamp unit 5 when the extension analyzer 4 is not provided on the analytic system 1. The mirror 12a and the condensing lenses 13a to 13c may be mounted on a mirror mounting portion 12c and lens mounting portions 13g to 13i respectively when the extension analyzer 4 is added to the analytic system 1. Thus, the cost for the lamp unit 5 can be reduced when the extension analyzer 4 is not provided on the analytic system 1.

The optical fiber members 17a and 17b are constituted of 21 optical fibers 17c and 21 optical fibers 17d respectively. Bundling members 17e and 17f bundle the 21 optical fibers 17c and the 21 optical fibers 17d respectively. The halogen lamp 11 includes a platelike filament 11a capable of emitting light components from both surfaces, as shown in FIG. 4. Thus, the halogen lamp 11 is so formed as to emit light components of the same characteristics from both surfaces of the platelike filament 11a. The platelike filament 11a, having small dispersion in the quantity of light in a photoirradiation region thereof, is so employed as to stabilize the quantities of light components (transmitted light components or scattered light components) obtained by applying light components to measurement samples, thereby suppressing measurement errors. The two mirrors 12a and 12b are provided for reflecting the light components emitted from the halogen lamp 11 and guiding the same to prescribed optical paths respectively. In other words, the mirrors 12a and 12b are arranged on both sides of the filament 11a, and located on positions correctly opposed to first and second surfaces of the filament 11a respectively. Further, the mirrors 12a and 12b are inclined with respect to the filament 11a, in order to change the traveling directions of the light components emitted from the filament 11a by 90° respectively.

The mirrors 12a and 12b reflect the light components emitted from the first and second surfaces of the platelike filament 11a of the halogen lamp 11 respectively. Thus, the light components reflected by the mirrors 12a 12b form two optical paths. The mirrors 12a and 12b are detachably mounted on the mirror mounting portion 12c and another mirror mounting portion 12d respectively, as shown in FIG. 3. The condensing lenses 13a to 13c are arranged on the path of the light component whose traveling direction is changed by the mirror 12a in this order from the side closer to the mirror 12a, as shown in FIG. 4. Similarly to the condensing lenses 13a to 13c, the condensing lenses 13d to 13f are arranged on the path of the light component whose traveling direction is changed by the mirror 12b in this order from the side closer to the mirror 12b. The two sets of condensing lenses 13a to 13c and 13d to 13f are so arranged that the directions of arrangement thereof are parallel to each other.

As shown in FIG. 4, the two sets of condensing lenses 13a to 13c and 13d to 13f condense the two light components reflected by the mirrors 12a and 12b for guiding the same to the optical fiber members 17a and 17b respectively, as shown in FIG. 4. The two light components reflected by the mirrors 12a and 12b are condensed by the condensing lenses 13a to 13c and 13d to 13f respectively, transmitted through any ones of optical filters 14b to 14f and guided to the optical fiber members 17a and 17b respectively. The condensing lenses 13a to 13c are detachably mounted on the lens mounting portions 13g to 13i respectively, as shown in FIG. 3. The condensing lenses 13d to 13f are also detachably mounted on corresponding lens mounting portions (not shown) respectively.

Figure 5:
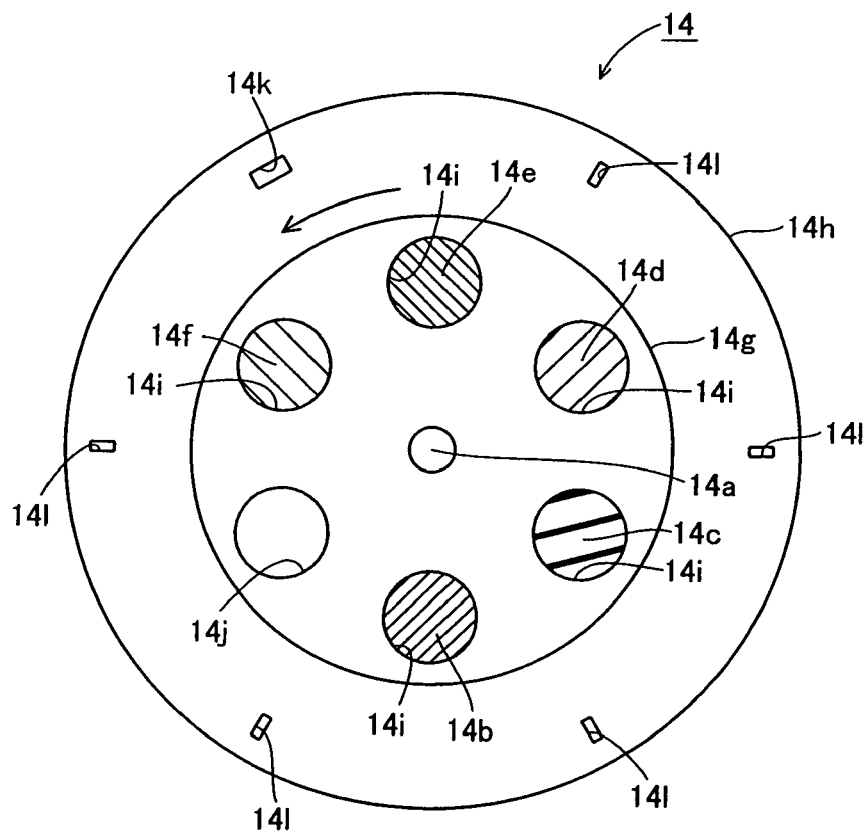
FIG. 5 is a plan view showing a filter portion of the lamp unit included in the analyzer according to the embodiment shown in FIG. 3.

According to this embodiment, the filter portion 14 of the lamp unit 5 is rotatable about a shaft 14a, as shown in FIG. 5. This filter portion 14 is constituted of a filter plate 14g provided with five optical filters 14b to 14f having different light transmission characteristics (transmission wavelengths) and a filter plate holding member 14h holding the filter plate 14g to expose both surfaces of the optical filters 14b to 14f. The filter plate 14g is fixed to the filter plate holding member 14h. This filter plate 14g is provided with five holes 14i for receiving the optical filters 14b to 14f respectively. The five optical filters 14b, 14c, 14d, 14e and 14f having different light transmission characteristics (transmission wavelengths) are set in the five holes 14i respectively. The filter plate 14g is further provided with a hole 14j, which is blocked not to transmit light. The holes 14i and 14j are provided at a prescribed angular interval (regular interval of 60° according to this embodiment) along the direction of rotation of the filter portion 14. The hole 14j is a preliminary hole for receiving an additional filter when the analytic system 1 requires this filter.

The optical filters 14b, 14c, 14d, 14e and 14f transmit light components having wavelengths of 340 nm, 405 nm, 575 nm, 660 nm and 800 nm respectively, while transmitting no light components of other wavelengths. Therefore, light components transmitted through the optical filters 14b, 14c, 14d, 14e and 14f have wavelength characteristics of 340 nm, 405 nm, 575 nm, 660 nm and 800 nm respectively.

The filter plate holding member 14h is so annularly formed that the filter plate 14g is arranged on a central hole portion thereof. The filter plate holding member 14h is circumferentially provided with six slits at a regular interval)(60°). One of the six slits is an origin slit 14k having a larger width than the remaining five slits 14l along the direction of rotation of the filter plate holding member 14h.

The origin slit 14k and the normal slits 14l are formed on intermediate angular positions (deviating from the holes 14i and 14j by)30° between the adjacent holes 14i and 14j at the regular interval of 60°. The motor 15 (see FIG. 3) is connected to the shaft 14a of the filter portion 14. Thus, the motor 15 drives the filter portion 14 to rotate about the shaft 14a.

According to this embodiment, the control board 6 (see FIG. 1) controls the motor 15 to continuously rotate the filter portion 14 when the lamp unit 5 emits a light component transmitted through any of the optical filters 14b to 14f. Following this rotation of the filter portion 14, the five optical filters 14b to 14f having different light transmission characteristics and the blocked hole 14j (see FIG. 5) are intermittently successively arranged on paths of the light components condensed by the condensing lenses 13a to 13c (see FIG. 4) and the condensing lenses 13d to 13f (see FIG. 4) respectively. Thus, the lamp unit 5 intermittently successively applies five types of light components having different wavelength characteristics.

The light transmission sensor 16 is provided for detecting passage of the origin slit 14k and the normal slits 14l following the rotation of the filter portion 14, as shown in FIG. 3. In other words, the sensor 16 is so set as to hold the filter portion 14 between a light source and a photoreceptive portion. This sensor 16 is provided in correspondence to a position passed by the origin slit 14k and the normal slits 14l.

Upon passage of the origin slit 14k and the normal slits 14l, therefore, the photoreceptive portion detects light from the light source through the slits 14k and 14l so that the sensor 16 outputs detection signals. Since the origin slit 14k is larger in width than the normal slits 14l, the detection signal output from the sensor 16 upon passage of the origin slit 14k has a longer output period than the detection signals output from the sensor 16 upon passage of the normal slits 14l. The detection signals output from the sensor 16 are transmitted to the control board 6 (see FIG. 1), so that a filter rotation monitoring portion 112b, described later, of the control board 6 monitors whether or not the filter portion 14 normally rotates on the basis of the detection signals received from the sensor 16.

The optical fiber members 17a and 17b are provided for guiding the light components received from the lamp unit 5 to measurement samples stored in the cuvettes 152 set on the second optical information acquisitive portions 80 of the analyzer 3 and the extension analyzer 4 respectively. As shown in FIG. 1, the optical fiber member 17a is so set as to extend from the lamp unit 5 toward the second optical information acquisitive portion 80 of the extension analyzer 4 through an extension connecting terminal 7 provided on the extension analyzer 4. Also the optical fiber member 17b is so set as to extend from the lamp unit 5 toward the second optical information acquisitive portion 80 of the analyzer 3. Thus, the single lamp unit 5 can supply light components to the second optical information acquisitive portions 80 of the analyzer 3 and the extension analyzer 4 respectively.

As shown in FIG. 4, each of the optical fiber members 17a and 17b is so formed as to receive a light component transmitted through any of the optical filters 14b to 14f from an end bundled by the bundling member 17e (17f). The 21 optical fibers 17c are so arranged as to supply light components to 20 receiving holes 81a and a reference light measurement hole 81b, described later, of the extension analyzer 4 (see FIG. 1) respectively. Also the 21 optical fiber members 17d are so arranged as to supply light components to 20 receiving holes 81a and a reference light measurement hole 81b, described later, of the analyzer 3 (see FIG. 1) respectively.

The cuvette supply portion 20 arranges the plurality of cuvettes 152, randomly introduced by a user, one by one on a position 152a. The cuvette transfer portion 60a transfers the cuvettes 152, each arranged on the position 152a, one by one to the rotary transport portion 30. The rotary transport portion 30 includes a discoidal table 30a, which is provided with a plurality of holes 152b for storing the cuvettes 152 and a plurality of holes 152c for storing reagent vessels (not shown) storing reagents added to specimens stored in the cuvettes 152. The rotary transport portion 30 transports the cuvettes 152 and the reagent vessels by rotating the table 30a.

The specimen injection arm 40 has a function of sucking specimens from the test tubes 150 transported to the suctional/injective position 2a (2b) while injecting the sucked specimens into the cuvettes 152 transferred by the rotary transport portion 30. The reagent injection arms 50 are provided for injecting the reagents stored in the reagent vessels (not shown) placed on the rotary transport portion 30 into the cuvettes 152 held on the rotary transport portion 30 thereby mixing the reagents into the specimens stored in the cuvettes 152. The cuvette transfer portion 60 is provided for transferring the cuvettes 152 between the rotary transport portion 30 and a cuvette receiving portion 81, described later, of the second optical information acquisitive portion 80.

Figure 6:
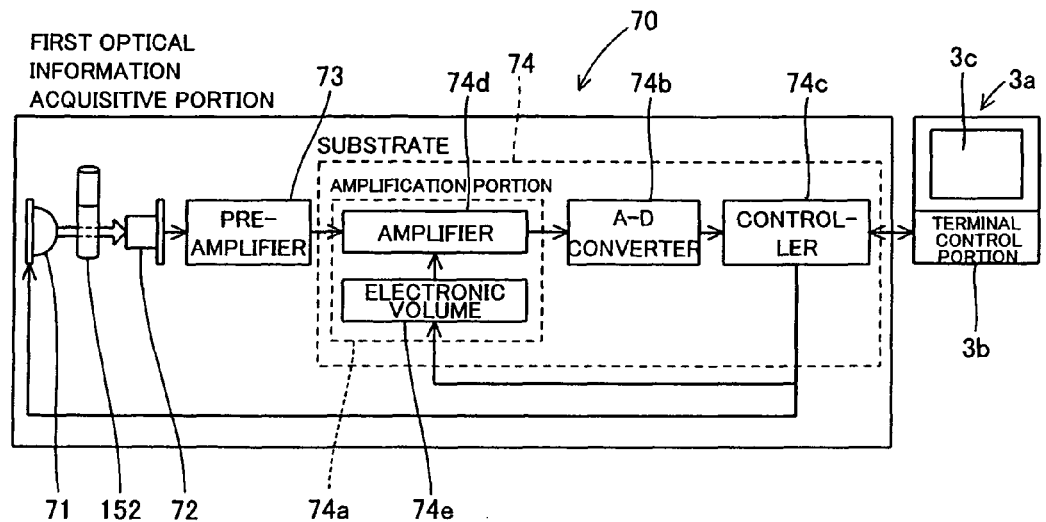
FIG. 6 is a block diagram for illustrating the structure of a first optical information acquisitive portion of the analyzer according to the embodiment shown in FIG. 1.

The first optical information acquisitive portion 70 is so formed as to acquire optical information from the specimens, in order to detect presence/absence, types and contents of interference substances (hemoglobin, chyle (lipid) and bilirubin) in the specimens not yet mixed with the reagents. The first optical information acquisitive portion 70 acquires the optical information before the second optical information acquisitive portion 80 optically measures the specimens. As shown in FIG. 6, the first optical information acquisitive portion 70 includes a light-emitting diode (LED) 71 serving as a light source, a photoelectric conversion element 72, a preamplifier 73 and a substrate 74. This first optical information acquisitive portion 70 acquires the optical information from the specimens by applying light components to the cuvettes 152 held on the rotary transport portion 30.

The light-emitting diode 71 is so provided as to apply light components to the cuvettes 152 held on the rotary transport portion 30. A controller 74c of the substrate 74 (see FIG. 6) controls the light-emitting diode 71 to periodically successively emit light components having three types of wavelength characteristics. More specifically, the light-emitting diode 71 periodically successively emits blue, green and red light components having wavelength characteristics of 430 nm, 565 nm and 627 nm respectively. The photoelectric conversion element 72 has a function of detecting the light components emitted from the light-emitting diode 71 and transmitted through the cuvettes 152 and converting the same to electric signals. The preamplifier 73 is provided for amplifying the electric signals received from the photoelectric conversion element 72.

The substrate 74 has a function of amplifying and digitizing the electric signals received from the photoelectric conversion element 72 and transmitting the same to the PC body 3b of the information processing terminal 3a. This substrate 74 is provided with an amplification portion 74a, an A-D converter 74b and a controller 74c, as shown in FIG. 6. The amplification portion 74a has an amplifier 74d and an electronic volume 74e. The amplifier 74d is provided for amplifying the electric signals received from the preamplifier 73. The amplifier 74d is so formed as to input a control signal from the controller 74c into the electronic volume 74e thereby controlling the gain (amplification factor) of the amplifier 74d. The A-D converter 74b is provided for converting the electric signals (analog signals) amplified by the amplifier 74d to digital signals.

The controller 74c is so formed as to change the gain (amplification factor) of the amplifier 74d in response to periodic change of the wavelength characteristics (430 nm, 565 nm and 627 nm) of the light components emitted from the light-emitting diode 71. Further, the controller 74c is electrically connected to the PC body 3b, for transmitting the digital signals converted by the A-D converter 74b to the PC body 3b. Thus, the PC body 3b analyzes the digital signals received from the first optical information acquisitive portion 70 thereby obtaining absorbance values (intensity levels of transmitted light components) of the specimens stored in the cuvettes 152 with respect to the three light components emitted from the light-emitting diode 71, while analyzing the presence/absence, types and contents of the interference substances in the specimens. On the basis of the results of analysis, the PC body 3b determines whether or not to measure the specimens with the second optical information acquisitive portion 80 and controls a method of analyzing detection signals from the second optical information acquisitive portion 80 and a method of displaying the results of analysis.

The second optical information acquisitive portion 80 has a function of warming the measurement samples prepared by adding the reagents to the specimens and detecting optical information from the measurement samples. This second optical information acquisitive portion 80 is constituted of the cuvette receiving portion 81 and a detection portion 82 (see FIG. 7) arranged under the cuvette receiving portion 81. The cuvette receiving portion 81 is provided with the 20 receiving holes 81a for receiving the cuvettes 152 and the reference light measurement hole 81b for measuring reference light without receiving any cuvette 152, as shown in FIG. 1. Further, the cuvette receiving portion 81 has a built-in warming mechanism (not shown) for warming the cuvettes 152 received in the receiving holes 81a.

Figure 7:
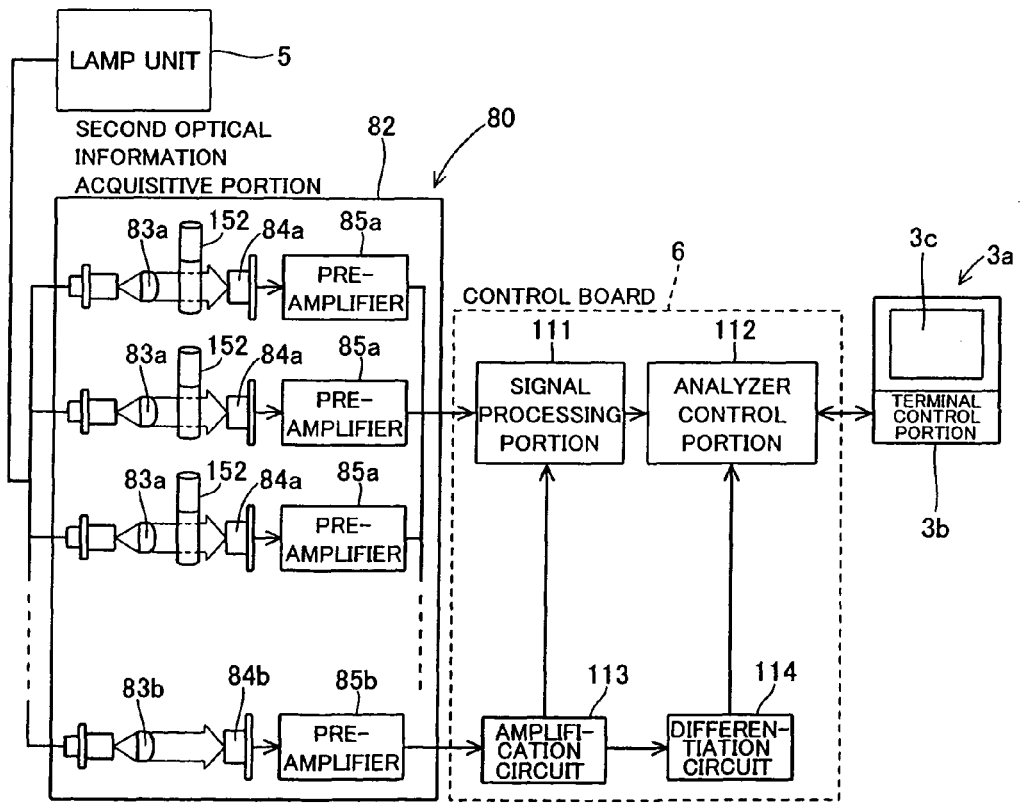
FIG. 7 is a block diagram for illustrating the structure of a second optical information acquisitive portion of the analyzer according to the embodiment shown in FIG. 1.
Figure 8:
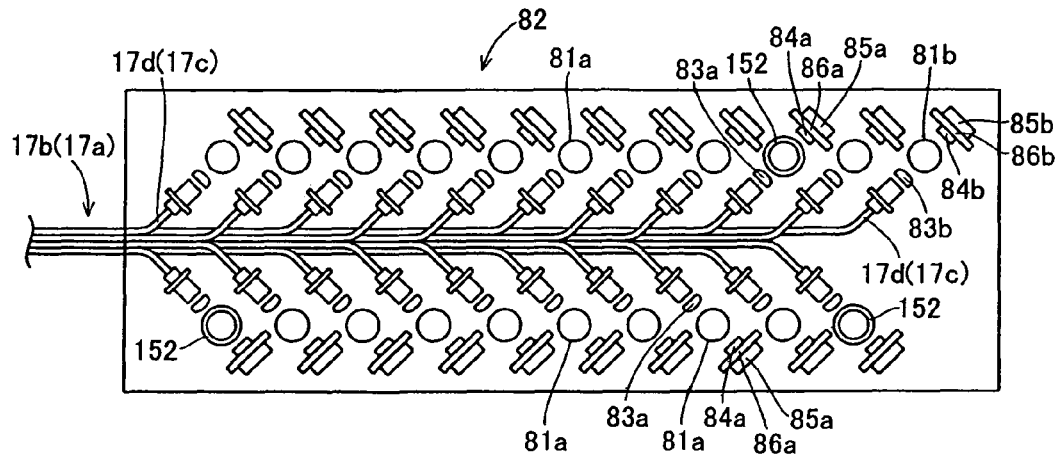
FIG. 8 is a schematic diagram showing the structure of a detection portion of the second optical information acquisitive portion of the analyzer according to the embodiment shown in FIG. 7.

The detection portion 82 is so formed as to optically measure the measurement samples stored in the cuvettes 152 received in the receiving holes 81a. As shown in FIGS. 7 and 8, the detection portion 82 is provided with collimator lenses 83a, photoelectric conversion elements 84a and preamplifiers 85a in correspondence to the receiving holes 81a receiving the cuvettes 152 respectively, and further provided with a reference light collimator lens 83b, a reference light photoelectric conversion element 84b and a reference light preamplifier 85b in correspondence to the reference light measurement hole 81b (see FIG. 1). The reference light collimator lens 83b, the reference light photoelectric conversion element 84b and the reference light preamplifier 85b are identical in structure to the collimator lenses 83a, the photoelectric conversion elements 84a and the preamplifiers 85a respectively.

As shown in FIG. 8, the collimator lenses 83a are set between ends of the optical fibers 17d (17c) guiding the light components received from the lamp unit 5 (see FIG. 1) and the corresponding receiving holes 81a. The collimator lenses 83a are provided for parallelizing the light components received from the optical fibers 17d (17c). The photoelectric conversion elements 84a are mounted on surfaces, closer to the receiving holes 81a, of substrates 86a opposite to the ends of the optical fibers 17d (17c) through the receiving holes 81a. The preamplifiers 85a are mounted on other surfaces of the substrates 86a opposite to the receiving holes 81a. The photoelectric conversion elements 84a have functions of detecting light components (hereinafter referred to as transmitted light components) transmitted through the measurement samples stored in the cuvettes 152 received in the receiving holes 81a upon photoirradiation and outputting electric signals (analog signals) corresponding to the detected transmitted light components. The preamplifiers 85a of the detection portion 82 are provided for amplifying the electric signals (analog signals) received from the photoelectric conversion elements 84a.

The reference light collimator lens 83b, the reference light photoelectric conversion element 84b, the reference light preamplifier 85b and a reference light substrate 86b provided on the detection portion 82 in correspondence to the reference light measuring hole 81b are identical in structure to the collimator lenses 83a, the photoelectric conversion elements 84a, the preamplifiers 85a and the substrates 86a provided on the detection portion 82 in correspondence to the receiving holes 81a respectively. The reference light photoelectric conversion element 84b is so formed as to directly receive a light component emitted from the corresponding optical fiber 17d (17c) and transmitted through the reference light collimator lens 83b as reference light. In other words, the reference light photoelectric conversion element 84b is so formed as to detect the reference light applied without through the cuvettes 152 storing the measurement samples and to output an electric signal (analog signal) corresponding to the detected reference light.

Figure 9:
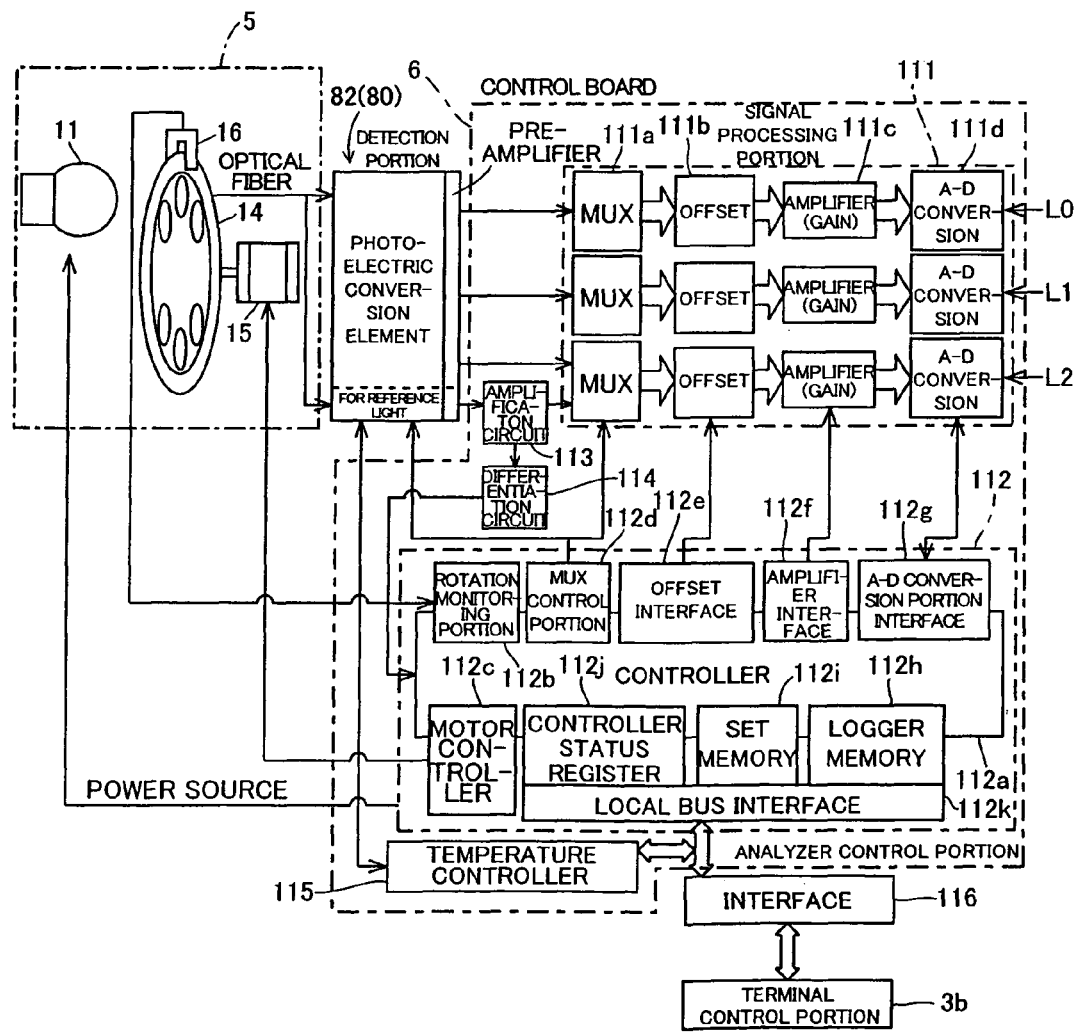
FIG. 9 is a block diagram for illustrating the components of the second optical information acquisitive portion and a control board of the analyzer according to the embodiment of the present invention.

The control board 6 is arranged under the second optical information acquisitive portion 80. This control board 6 has a function of controlling operations of the analyzer 3 and the lamp unit 5 while processing and storing the optical information (electric signals) received from the second optical information acquisitive portion 80. As shown in FIGS. 7 and 9, the control board 6 is provided with the signal processing portion 111, the control portion 112, an amplification circuit 113, a differentiation circuit 114 and a temperature controller 115. The signal processing portion 111 is provided for processing the signals output from the photoelectric conversion elements 84*a* detecting the transmitted light components when the lamp unit 5 applies the light components to the measurement samples. As shown in FIG. 9, this signal processing portion 111 has three multiplexers (MUX) 111*a*, three offset circuits 111*b*, three amplifiers 111*c* and three A-D conversion portions 111*d*. The first multiplexer 111*a*, the first offset circuit 111*b*, the first amplifier 111*c* and the first A-D conversion portion 111*d* constitute a signal processing line L0. The signal processing portion 111 is also provided with signal processing lines L1 and L2 similar in structure to the signal processing line L0. In other words, the signal processing portion 111 is provided with the three signal processing lines L0 to L2 for processing the plurality of analog signals received from the detection portion 82.

Figure 10:
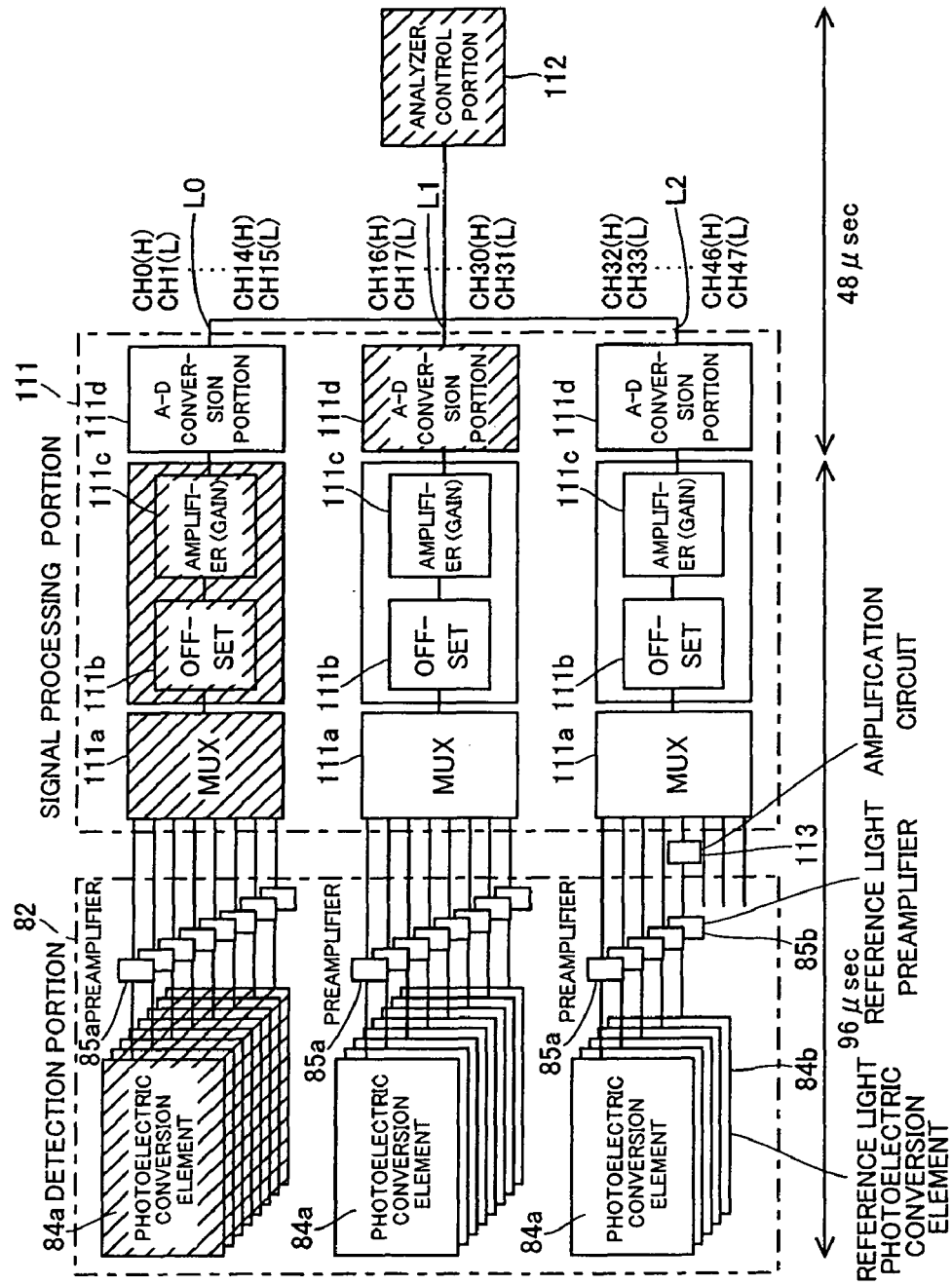
FIG. 10 is a block diagram for illustrating the structures of the detection portion and a signal processing portion of the analyzer according to the embodiment of the present invention.

As shown in FIG. 10, the multiplexers 111*a* are connected to the plurality of preamplifiers 85*a* (reference light preamplifier 85*b*). These multiplexers 111*a* are so formed as to select the plurality of analog signals received from the plurality of photoelectric conversion elements 84*a* (reference light photoelectric conversion element 84*b*) through the preamplifiers 85*a* (reference light preamplifier 85*b*) one by one and to successively output the same to the offset circuits 111*b*. The offset circuits 111*b* have functions of correcting the signals received from the multiplexers 111*a*. More specifically, the offset circuits 111*b* are supplied with offset values corresponding to the receiving holes 81*a* and the reference light measurement hole 81*b* employed for measurement respectively from the control portion 112 (see FIG. 9). The offset circuits 111*b* subtract these offset values from the signals corresponding to the transmitted light components received from the multiplexers 111*a*, thereby correcting the signals corresponding to the transmitted light components received from the multiplexers 111*a*.

The amplifiers 111*c* have functions of amplifying the analog signals received from the offset circuits 111*b*. The control portion 112 controls the gains (amplification factors) of these amplifiers 111*c*, to be switchable between low gains and high gains higher than the low gains. Signals of the low gains (amplification factors) and the high gains (amplification factors) amplified by the amplifiers 111*c* are input in the A-D conversion portions 111*d* at different timings. The A-D conversion portions 111*d*, connected to the amplifiers 111*c* respectively, are provided for converting processed analog signals amplified to the signals (analog signals) of the low and high gains by the amplifiers 111*c* to digital signals (data).

According to this embodiment, the A-D conversion portions 111*d* output 48 data (16 data per A-D conversion portion 111*d*) corresponding to channels CH0 to CH47 respectively, as shown in FIG. 10. Among these channels CH0 to CH47, the data of 42 channels CH0 to CH41 correspond to data based on the electric signals obtained from the photoelectric conversion elements 84*a* and the reference light photoelectric conversion element 84*b* respectively. In other words, the amplifiers 111*c* of the signal processing portion 111 amplify 20 data obtained from 20 photoelectric conversion elements 84*a* to 40 data with the low and high gains (amplification factors). One of the amplifiers 111*c* of the signal processing portion 111 (see FIG. 9) amplifies single data obtained from the reference light photoelectric conversion element 84*b* to two data with the low and high gains (amplification factors). The data of the channels CH0 to CH41 correspond to 42 data obtained by totalizing the aforementioned 40 data and the two data corresponding to the reference light. The remaining six channels CH42 to CH47 are preliminary channels not used in this embodiment, and data of these channels CH42 to CH47 do not correspond to the electric signals from the photoelectric conversion elements 84*a* and the reference light photoelectric conversion element 84*b*.

The control portion 112 has functions of controlling the operations of the analyzer 3 and acquiring and storing the digital signals (data) received from the A-D conversion portions 111*d*. As shown in FIG. 9, this control portion 112 includes a controller 112*a*, the filter rotation monitoring portion 112*b*, a motor controller 112*c*, a multiplexer control portion 112*d*, an offset interface 112*e*, an amplifier interface 112*f*, an A-D conversion portion interface 112*g*, a logger memory 112*h*, a set memory 112*i*, a controller status register 112*j* and a local bus interface 112*k*.

The controller 112*a* has a function of unifying various control operations with the control portion 112. The filter rotation monitoring portion 112*b* is provided for monitoring whether or not the filter portion 14 of the lamp unit 5 normally rotates. This filter rotation monitoring portion 112*b* is so formed as to receive the detection signals from the sensor 16 detecting passage of the origin slit 14*k* (see FIG. 5) and the normal slits 14*l* following rotation of the filter portion 14. The filter rotation monitoring portion 112*b* monitors whether or not the filter portion 14 normally rotates by monitoring the time intervals of the detection signals for the origin slit 14*k* (see FIG. 5) and the normal slits 14*l* (see FIG. 5) output from the sensor 16 and the frequency of the detection signals for the normal slits 14*l* output between pairs of detection signals for the origin slit 14*k* output from the sensor 16. The motor controller 112*c* has a function of controlling the rotational frequency of the motor 15 rotating the filter portion 14. The multiplexer control portion 112*d* has a function of controlling operations of the multiplexers 111*a*. More specifically, the multiplexer control portion 112*d* controls the operations of the plurality of multiplexers 111*a* to select the analog signals at different times respectively.

The controller 112*a* is so formed as to control operations of the offset circuits 111*b*, the amplifiers 111*c* and the A-D conversion portions 111*d* of the signal processing portion 111 through the offset interface 112*e*, the amplifier interface 112*f* and the A-D conversion portion interface 112*g* respectively, as shown in FIG. 9. More specifically, the controller 112*a* supplies prescribed offset values to the offset circuits 111*b* through the offset interface 112*e*, while controlling the offset circuits 111*b* to perform correction processing by subtracting the offset values from the signals received from the multiplexers 111*a*. The controller 112*a* controls the amplifiers 111*c* between the low and high gains through the amplifier interface 112*f*, while controlling the amplifiers 111*c* to amplify the signals received from the offset circuits 111*b*. Further, the controller 112*a* controls the A-D conversion portions 111*d* to convert the signals (analog signals) received from the amplifiers 111*c* to digital signals through the A-D conversion portion interface 112*g*. The logger memory 112*h* receives and stores the digital signals (data) acquired by the A-D conversion portions 111*d* through the A-D conversion portion interface 112*g* and the controller 112*a*. At this time, the controller 112*a* controls operations of the A-D conversion portions 111*d* through the A-D conversion portion interface 112*g*, not to overlap the periods for outputting the digital signals respectively with each other.

The controller 112a also has a function of switching that executing processing among the multiplexers 111a, the offset circuits 111b, the amplifiers 111c and the A-D conversion portions 111d of the signal lines L0 to L2 and the logger memory 112h, so that the A-D conversion portion 111d of another signal processing line L1, L2 or L0 performs conversion processing with the corresponding A-D conversion portion 116d and the logger memory 112h of the control portion 112 stores data while the multiplexer 111a, the offset circuit 111b and the amplifier 111c of a prescribed signal processing line L0, L1 or L2 process the corresponding analog signals. This point is described later in more detail with reference to an analytic operation.

Figure 11:
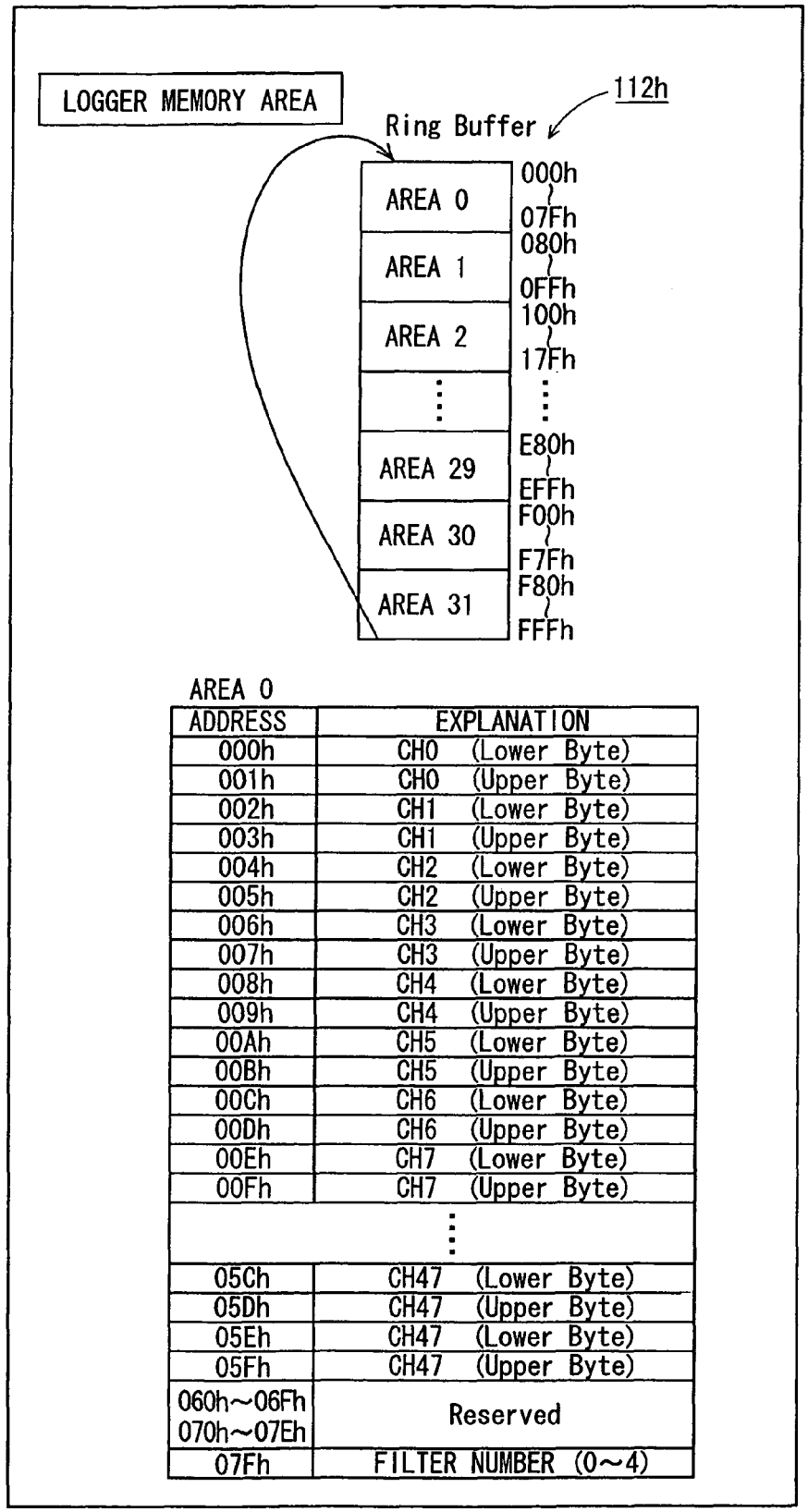
FIG. 11 is a diagram for illustrating the structure of a logger memory of the control board of the analyzer according to the embodiment of the present invention.

The logger memory 112h is provided for storing the digital signals (data) corresponding to the analog signals output from the photoelectric conversion elements 84a. As shown in FIG. 11, the logger memory 112h is constituted of 32 areas 0 to 31 in units of 128 bytes. The areas 0 to 31 store data corresponding to the light components transmitted through the five optical filters 14b to 14f (see FIG. 5) and data corresponding to the blocked hole 14j respectively. Every rotation of the filter portion 14 results in data corresponding to the light components transmitted through the five optical filters 14b to 14f having different light transmission characteristics. The logger memory 112h (see FIG. 11) stores these data successively from the area 0. The logger memory 112h stores "0" in every sixth area as the data corresponding to the hole 14j. Thus, the logger memory 112h uses six areas every rotation (about 100 msec.) of the filter portion 14. After using the areas 0 to 31 up to the final area 31, the logger memory 112h returns to the area 0 for overwriting data.

Each of the areas 0 to 31 of the logger memory 112h has 128 addresses. For example, the area 0 has 128 addresses 000h to 00Fh, 010h to 01Fh, 020h to 02Fh, 030h to 03Fh, 040h to 04Fh, 050h to 05Fh, 060h to 06Fh and 070h to 07Fh. Further, the area 0 is so formed as to store the data of the aforementioned channels CH0 to CH47 (see FIG. 10) in the 96 addresses 00h to 05Fh. Each of the data of the channels CH0 to CH47 is stored in two addresses. According to this embodiment, the channels CH42 to 47 output no data as hereinabove described, so that addresses corresponding to these channels CH42 to 47 store no data.

The addresses 060h to 06Fh and 070h to 07Fh in the area 0 of the logger memory 112h shown in FIG. 11 are preliminary addresses storing no data in this embodiment. The area 0 stores filter numbers (0 to 4) in the final address 07Fh. These filter numbers (0 to 4) are employed for identifying the five optical filters 14b to 14f (see FIG. 5) respectively. The optical filters 14b to 14f can be identified by detecting the timing of passage of the origin slit 14k. The area 0 stores the filter numbers (0 to 4) corresponding to the five optical filters 14b to 14f in the address 07Fh, thereby identifying the optical filter (one of 14b to 14f) through which the light component corresponding to the data stored in the area 0 has been transmitted.

The set memory 112i shown in FIG. 9 is provided for storing set values such as the offset values supplied to the offset circuits 111b and the gains (amplification factors) supplied to the amplifiers 111c. The controller status register 112j is provided for temporarily storing information such as whether or not the filter portion 14 normally rotates, presence/absence of errors in analog-to-digital conversion by the A-D conversion portions 111d, the status of data acquisition by the PC body 3b from the logger memory 112h and presence/absence of an instruction for starting measurement from the PC body 3b. The control portion 112 has a function of transmitting the data (optical information) of the measurement samples stored in the logger memory 112h to the PC body 3b through the local bus interface 112k and an interface 116.

The amplification circuit 113 of the control board 6 shown in FIG. 9 has a function of receiving the signal output from the reference light photoelectric conversion element 84b (see FIG. 10) through the reference light preamplifier 85b and amplifying the received signal.

Figure 12:
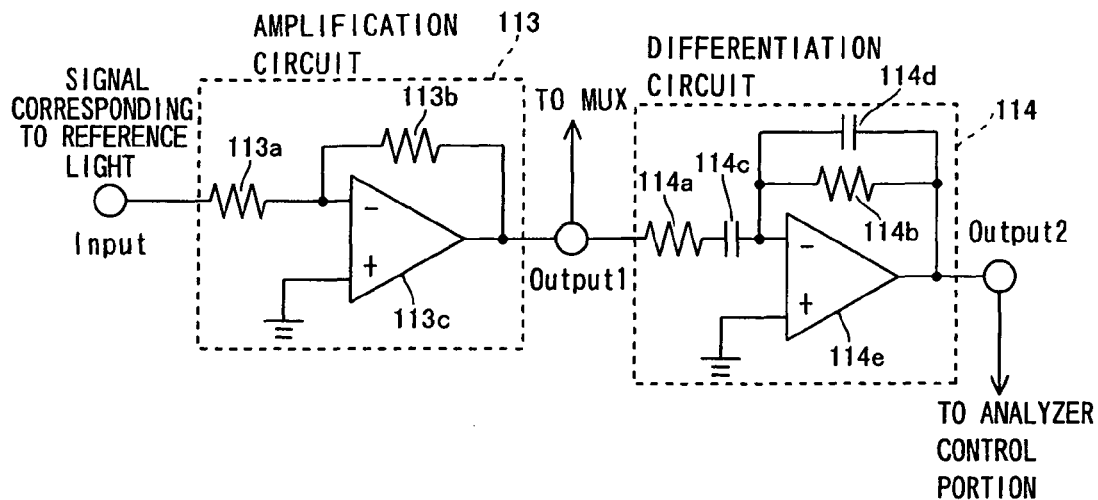
FIG. 12 is a circuit diagram showing the circuit structures of an amplification circuit and a differentiation circuit of the control board of the analyzer according to the embodiment of the present invention.

As shown in FIG. 12, this amplification circuit 113 is constituted of two resistors 113a and 113b and an operational amplifier 113c. A first end of the resistor 113a receives the signal corresponding to the reference light from the reference light preamplifier 85b, while a second end thereof is connected to an inverted input terminal of the operational amplifier 113c. The resistor 113b is connected between an output terminal and the inverted input terminal of the operational amplifier 113c. A non-inverted input terminal of the operational amplifier 113c is grounded. The multiplexers 111a of the signal processing portion 111 (see FIG. 9) and the differentiation circuit 114 receive an output of the operational amplifier 113c.

The differentiation circuit 114 of the control board 6 has a function of generating a differential signal of the signal (hereinafter referred to as a reference signal) corresponding to the reference light received from the amplification circuit 113. As shown in FIG. 12, this differentiation circuit 114 is constituted of two resistors 114a and 114b, two capacitors 114c and 114d and an operational amplifier 114e. A first end of the resistor 114a receives the reference signal from the amplification circuit 113, while a second end thereof is connected to a first electrode of the capacitor 114c. A second electrode of the capacitor 114c is connected to an inverted input terminal of the operational amplifier 114e. Both of the resistor 114b and the capacitor 114d are connected between an output terminal and the inverted input terminal of the operational amplifier 114e. A non-inverted input terminal of the operational amplifier 114e is grounded. The controller 112a of the control portion 112 (see FIG. 9) receives an output of the operational amplifier 114e through a comparator (not shown).

The temperature controller 115 of the control board 6 show in FIG. 9 has a function of controlling the temperature of the cuvette receiving portion 81 (see FIG. 1) receiving the cuvettes 152 by controlling another warming mechanism (not shown) stored in the second optical information acquisitive portion 80. As shown in FIG. 9, the temperature controller 115 is so formed as to control warming with the warming mechanism (not shown) of the second optical information acquisitive portion 80 in response to a set temperature (about 37° C.) received from the PC body 3b through the interface 116.

The outline of control of the analyzer 3 with the PC body 3b is now described with reference to FIGS. 2, 3 and 13. The analyzer 3 and the extension analyzer 4 are identical in control to each other, and hence the control of the analyzer 3 is described in the following.

The analytic system 1 starts the information processing terminal 3a, the body of the analyzer 3 and the extension analyzer 4 by supplying power thereto.

Figure 13:
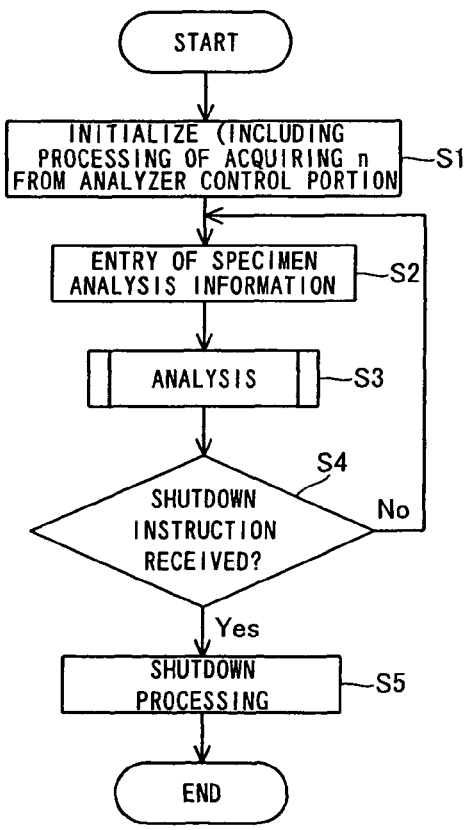
FIG. 13 is a flow chart showing the outline of a control method by a PC body of the analyzer according to the embodiment of the present invention.

Upon this power supply, the PC body 3b performs initialization at a step S1 shown in FIG. 13. In this initialization, the PC body 3b initializes software stored therein and performs processing of acquiring n clocks described later from the control portion 112 of the analyzer 3. Upon power supply to the body of the analyzer 3, the halogen lamp 11 of the lamp unit 5 (see FIG. 3) applies light while the filter portion 14 starts continuously rotating at a rotational speed of 10 revolutions/sec. in the initialization at the step S1. The halogen lamp 11 continuously applies light and the filter portion 14 continuously rotates until the body of the analyzer 3 is turned off. At a step S2, the PC body 3b accepts entry of specimen analysis information by the user. In other words, the user inputs information in columns of specimen numbers and measurement items of a specimen analysis list output on the display portion 3c of the information processing terminal 3a (see FIG. 2) through the keyboard 3d of the information processing terminal 3a. The PC body 3b preserves the specimen analysis information.

At a step S3, the PC body 3b instructs analysis, so that the analyzer 3 performs the analysis. At a step S4, the PC body 3b determines whether or not a shutdown instruction for the analytic system 1 has been received. When determining that no shutdown instruction for the analytic system 1 has been received at the step S4, the PC body 3b returns to the step S2 for accepting entry of another specimen analysis information by the user. When determining that a shutdown instruction for the analytic system 1 has been received at the step S4, on the other hand, the PC body 3b performs shutdown processing at a step S5. According to this shutdown processing, the analytic system 1 automatically enters an OFF-state, thereby completing the operation thereof.

A method of calculating the n clocks with the control portion 112 is now described with reference to FIGS. 3, 7 to 9, 14 and 15.

Figure 15:
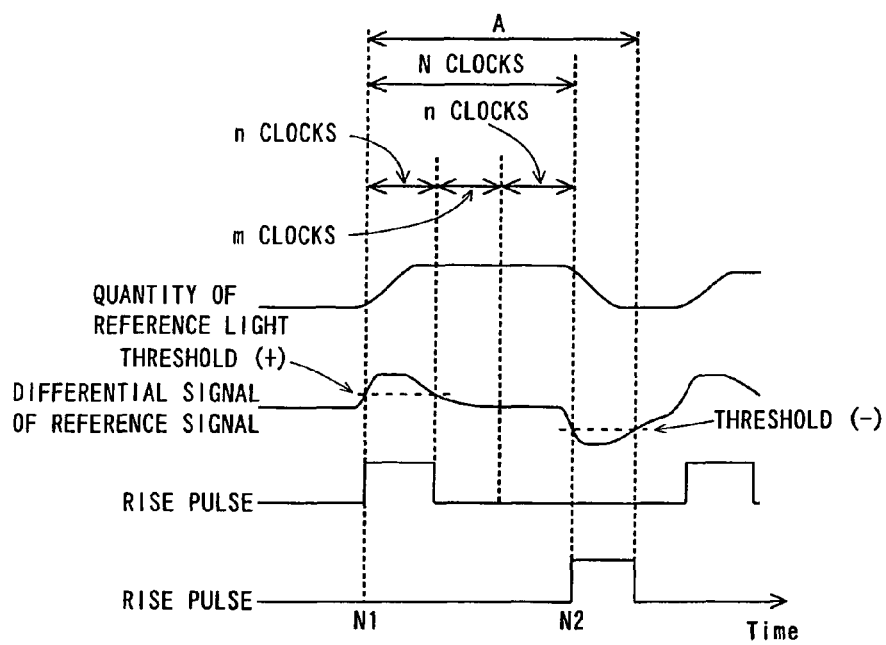
FIG. 15 is a waveform diagram showing changes in the quantity of reference light and a differential signal of a reference signal employed in the method of calculating n clocks shown in FIG. 14.

As shown in FIG. 15, the quantity of the reference light incident upon the reference light photoelectric conversion element 84b (see FIG. 8) from the lamp unit 5 changes along a waveform shown as "QUANTITY OF REFERENCE LIGHT" during the continuous rotation of the filter portion 14 (see FIG. 3). Referring to FIG. 15, symbol A denotes a period when any one of the optical filters 14b to 14f of the rotating filter portion 14 is arranged on the path of the corresponding light component from the halogen lamp 11 in the lamp unit 5 (see FIG. 3). When the aforementioned one of the optical filters 14b to 14f approaches the path of the corresponding light component from the halogen lamp 11 in this period A, the quantity of the reference light gradually increases. Thereafter the path of the corresponding light component from the halogen lamp 11 completely falls into the aforementioned one of the optical filters 14b to 14f, so that the quantity of the reference light is constant. When the aforementioned one of the optical filters 14b to 14f thereafter starts deviating from the path of the corresponding light component from the halogen lamp 11, the quantity of the reference light starts to gradually decrease. When the aforementioned one of the optical filters 14b to 14f completely deviates from the path of the corresponding light component from the halogen lamp 11, the quantity of the reference light reaches zero.

As shown in FIG. 7, the reference light photoelectric conversion element 84b converts the reference light to an electric signal, so that the reference light preamplifier 85b and the amplification circuit 113 amplify this electric signal. The amplification circuit 113 outputs a signal (hereinafter referred to as a reference signal) corresponding to the reference light, so that the differentiation circuit 114 receives this reference signal. The differentiation circuit 114 generates a differential signal of the reference signal having a waveform shown as "DIFFERENTIAL SIGNAL OF REFERENCE SIGNAL" in FIG. 15. The control portion 112 receives this differential signal of the reference signal from the differentiation circuit 114 (see FIG. 9) through the comparator (not shown).

Figure 14:
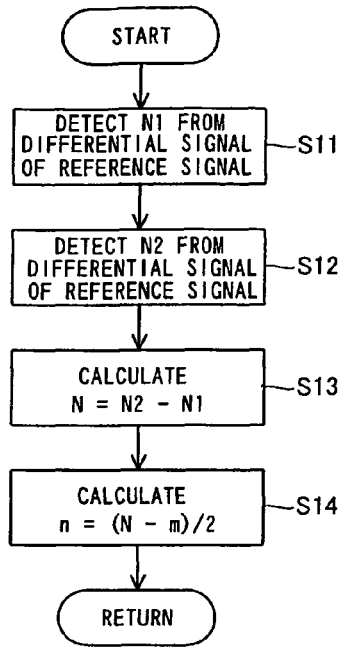
FIG. 14 is a flow chart showing a method of calculating n clocks acquired by the PC body with a control portion in initialization shown at a step S1 in FIG. 13.

At a step S11 shown in FIG. 14, the control portion 112 detects a clock number N1 at a point of time when the differential signal of the reference signal reaches a prescribed positive threshold (+). More specifically, the differential signal of the reference signal rises following increase of the quantity of the reference light, as shown in FIG. 15. In response to the differential signal reaching the prescribed positive threshold (+), the comparator (not shown) receiving the differential signal from the differentiation circuit 114 (see FIG. 9) outputs a pulse signal rising to a high level. The controller 112a of the control portion 112 receives this pulse signal, and detects the clock number N1 at the point of time when the pulse signal has risen to the high level. Thus, the controller 112a detects the clock number N1 at the point of time when the differential signal of the reference signal reaches the prescribed positive threshold (+).

Thereafter the quantity of the reference light further increases and reaches a prescribed constant value, as shown in FIG. 15. Thereafter the quantity of the reference light gradually decreases. Following this, the differential signal of the reference signal gradually falls. At a step S12 shown in FIG. 14, the control portion 12 detects a clock number (N2) at a point of time when the differential signal of the reference signal reaches a prescribed negative threshold (−). More specifically, the comparator (not shown) receiving the differential signal from the differentiation circuit 114 (see FIG. 9) outputs a pulse signal rising to a high level in response to the differential signal of the reference signal gradually falling and reaching the prescribed negative threshold (−). The controller 112a of the control portion 112 receives this pulse signal, and detects the clock number N2 at the time when the pulse signal has risen to the high level. Thus, the controller 112a of the control portion 112 detects the clock number N2 at the time when the differential signal of the reference signal reaches the prescribed negative threshold (−).

At a step S13 in FIG. 14, the control portion 112 calculates the number of clocks (N clocks) counted between the clock numbers N1 and N2 according to a formula n=N2−N1. At a step S14, the control portion 112 calculates the clock number (n clocks) for deciding the timing for starting acquiring the signals corresponding to the light components transmitted through the measurement samples according to a formula n=(N−m)/2, where m represents the number of clocks previously set as a proper period necessary for the control portion 112 for acquiring the signals corresponding to the light components transmitted through the measurement samples. According to this embodiment, the control portion 112 calculates the timing for starting acquiring the signals corresponding to the transmitted light components with the reference light not influenced by the measurement samples etc. As understood from FIG. 15, the control portion 112 can acquire signals in a period where the quantities of the light components applied from the lamp unit 5 are stable by acquiring the signals corresponding to the light components transmitted through the measurement samples from the detection portion 82 for the period of m clocks with the multiplexers 111a after n clocks calculated in the aforementioned manner from the clock N1.

The aforementioned processing at the step S3 in FIG. 13 is now described in detail with reference to FIGS. 1, 2, 5 to 11, 13 and 16 to 18. At a step S21 shown in FIG. 16, the PC body 3b instructs primary measurement. Thus, the aforementioned first optical information acquisitive portion 70 measures interference substances in the specimens. The PC body 3b receives the optical information acquired by the first optical information acquisitive portion 70 through the controller 74c.

At a step S22, the PC body 3b analyzes the received optical information, and determines whether or not the primarily measured specimens are to be subjected to secondary measurement with the second optical information acquisitive portion 80 on the basis of the results of the analysis. When determining that the specimens are not to be subjected to secondary measurement with the second optical information acquisitive portion 80, the PC body 3*b* makes the display portion 3*c* display a message indicating that it is difficult to perform reliable analysis due to remarkable influence by interference substances contained in these specimens (step S28). When determining that the specimens are to be subjected to secondary measurement at the step S22, on the other hand, the PC body 3*b* instructs suction of the specimens at a step S23. Thus, the specimen injection arm 40 sucks the specimens from the cuvettes 152 held on the rotary transport portion 30.

At a step S24, the PC body 3*b* instructs preparation of measurement samples. Thus, the specimen injection arm 40 injects the sucked specimens into the plurality of cuvettes 152 while the reagent injection arms 50 add the reagents for starting blood coagulation contained in the reagent vessels (not shown) to the specimens stored in the plurality of cuvettes 152 in the analyzer 3. Thus, the analyzer 3 prepares the measurement samples. Then, the cuvette transfer portion 60 moves the cuvettes 152 storing the measurement samples toward the receiving holes 81*a* of the cuvette receiving portion 81 of the second optical information acquisitive portion 80.

At a step S25, the PC body 3*b* instructs secondary measurement. Thus, the analyzer 3 starts secondary measurement of the measurement samples. This secondary measurement is now described in detail.

As hereinabove described, the lamp unit 5 intermittently successively applies the five types of light components having different wavelength characteristics (340 nm, 405 nm, 575 nm, 660 nm and 800 nm) respectively to the cuvettes 152 moved toward the receiving holes 81*a*. The light components transmitted through the cuvettes 152 are converted to digital data through the photoelectric conversion elements 84*a*, the preamplifiers 85*a*, the multiplexers 111*a*, the offset circuits 111*b*, the amplifiers 111*c* and the A-D conversion portions 111*d* and stored in the logger memory 112*h*.

Operations of the signal processing portion 111 are now described with reference to FIG. 10.

The three signal processing lines L0 to L2 constituted of the multiplexers 111*a*, the offset circuits 111*b*, the amplifiers 111*c* and the A-D conversion portions 111*d* partially parallelly process the electric signals with the multiplexers 111*a*, the offset circuits 111*b*, the amplifiers 111*c* and the A-D conversion portions 111*d*. As shown in FIG. 10, the signal processing line L0 processes the corresponding electric signals with the multiplexer 111*a*, the offset circuit 111*b* and the amplifier 111*c*, the signal processing line L1 converts the corresponding electric signals with the A-D conversion portion 111*d* and the logger memory 112*h* (see FIG. 9) of the control portion 112 stores data in parallel with each other. Similarly, the signal processing line L1 processes the corresponding electric signals with the multiplexer 111*a*, the offset circuit 111*b* and the amplifier 111*c*, the signal processing line L2 converts the corresponding electric signals with the A-D conversion portion 111*d* and the logger memory 112*h* (see FIG. 9) of the control portion 112 stores data in parallel with each other. Further, the signal processing line L2 processes the corresponding electric signals with the multiplexer 111*a*, the offset circuit 111*b* and the amplifier 111*c*, the signal processing line L0 converts the corresponding electric signals with the A-D conversion portion 111*d* and the logger memory 112*h* (see FIG. 9) of the control portion 112 stores data in parallel with each other.

Figures 17, 18:
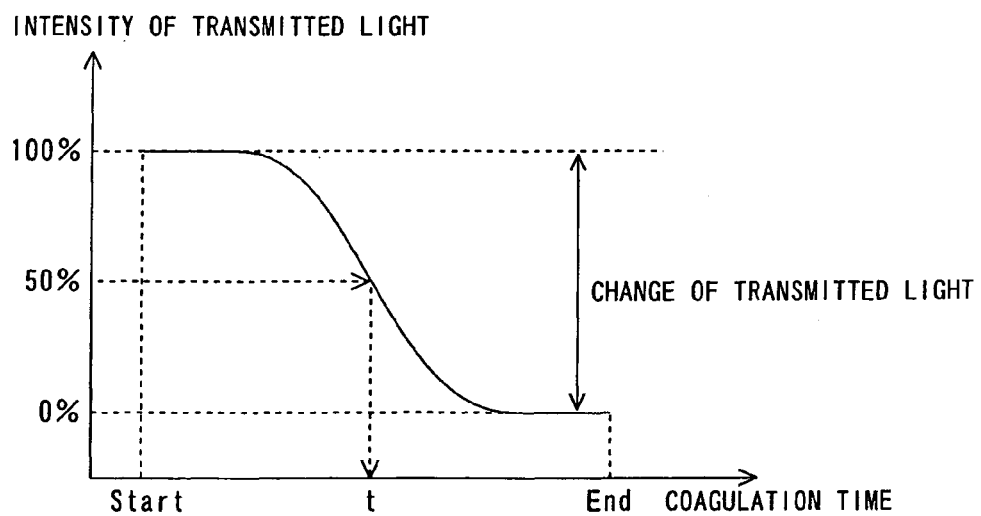
FIG. 17 illustrates a signal processing method in the signal processing portion of the analyzer according to the embodiment of the present invention.
FIG. 18 is a graph showing a coagulation curve created by the analytic system according to the embodiment of the present invention.

The signal processing portion 111 partially parallelly processes the electric signals in units of 48 μsec. by successively using the three signal processing lines L0 to L2, as shown in FIG. 17. More specifically, the signal processing line L0 performs switching to the channel CH0 with the multiplexer 111*a*, correction with the offset circuit 111*b* and amplification with the amplifier 111*c* at a step 0 shown in FIG. 17. At this step 0, the signal processing lines L1 and L2 are in states waiting for stabilization of the corresponding electric signals (signal wait states), to process no electric signals. At a step 1 in FIG. 17, the signal processing line L1 performs switching to the channel CH6 with the multiplexer 111*a*, correction with the offset circuit 111*b* and amplification with the amplifier 111*c*. At this step 1, the signal processing lines L0 and L1 are in states waiting for stabilization of the corresponding electric signals, to process no electric signals.

At a step 2 in FIG. 17, the signal processing line L0 performs A-D conversion of the electric signal of the channel CH0 with the A-D conversion portion 111*d*, the logger memory 112*h* stores data and the signal processing line L2 performs switching to the channel CH32 with the multiplexer 111*a*, correction with the offset circuit 111*b* and amplification with the amplifier 111*c* in parallel with each other. At the step 2, the signal processing line L1 is in a state waiting for stabilization of the corresponding electric signals, not to process the electric signals.

At a step 3 in FIG. 17, the signal processing line L0 performs switching to the channel CH1 with the multiplexer 111*a*, correction with the offset circuit 111*b* and amplification with the amplifier 111*c*, the signal processing line L1 performs A-D conversion of the electric signal of the channel CH16 with the A-D conversion portion 111*d* and the logger memory 112*h* stores data in parallel with each other. At this step 3, the signal processing line L2 is in a state waiting for stabilization of the corresponding electric signals, not to process the electric signals.

At a step 4 in FIG. 17, the signal processing line L1 performs switching to the channel CH17 with the multiplexer 111*a*, correction with the offset circuit 111*b* and amplification with the amplifier 111*c*, the signal processing line L2 performs A-D conversion of the electric signal of the channel CH32 with the A-D conversion portion 111*d* and the logger memory 112*h* stores data in parallel with each other. At this step 4, the signal processing line L0 is in a state waiting for stabilization of the corresponding electric signals, not to process the electric signals.

The signal processing lines L0 to L2 repetitively perform parallel processing similar to that through the aforementioned steps 2 to 4 up to a step 49 while switching the channels for signal processing. At a step 50, the signal processing line L2 performs switching to the channel CH32 with the multiplexer 111*a*, correction with the offset circuit 111*b* and amplification with the amplifier 111*c*. At the step 50, the signal processing lines L0 and L1 are in states waiting for stabilization of the corresponding electric signals, not to process the electric signals.

All output signals of the multiplexers 111*a*, the offset circuits 111*b* and the amplifiers 111*c* are unstable immediately after signal processing. According to this embodiment, the aforementioned periods for waiting for stabilization of the electric signals are so provided as to prevent such unstable signals from application to analysis of analytes.

The signal processing lines L0 to L2 process the electric signals of all channels CH0 to CH47 through the 51 steps 0 to 50 in the aforementioned manner. The signal processing lines L0 to L2 process the electric signals through the 51 steps 0 to 50 in a period of 2.45 msec. (=48 μsec.×51 steps). Further, the signal processing lines L0 to L2 process the electric signals through the 51 steps 0 to 50 once in a period of data acquisitive processing of m clocks described later.

As hereinabove described, the logger memory 112h stores data in prescribed addresses, for specifying the optical filters and the channels transmitting the light components received from the halogen lamp 11. The logger memory 112h transmits the data stored therein to the PC body 3b at prescribed timing.

Figure 16:
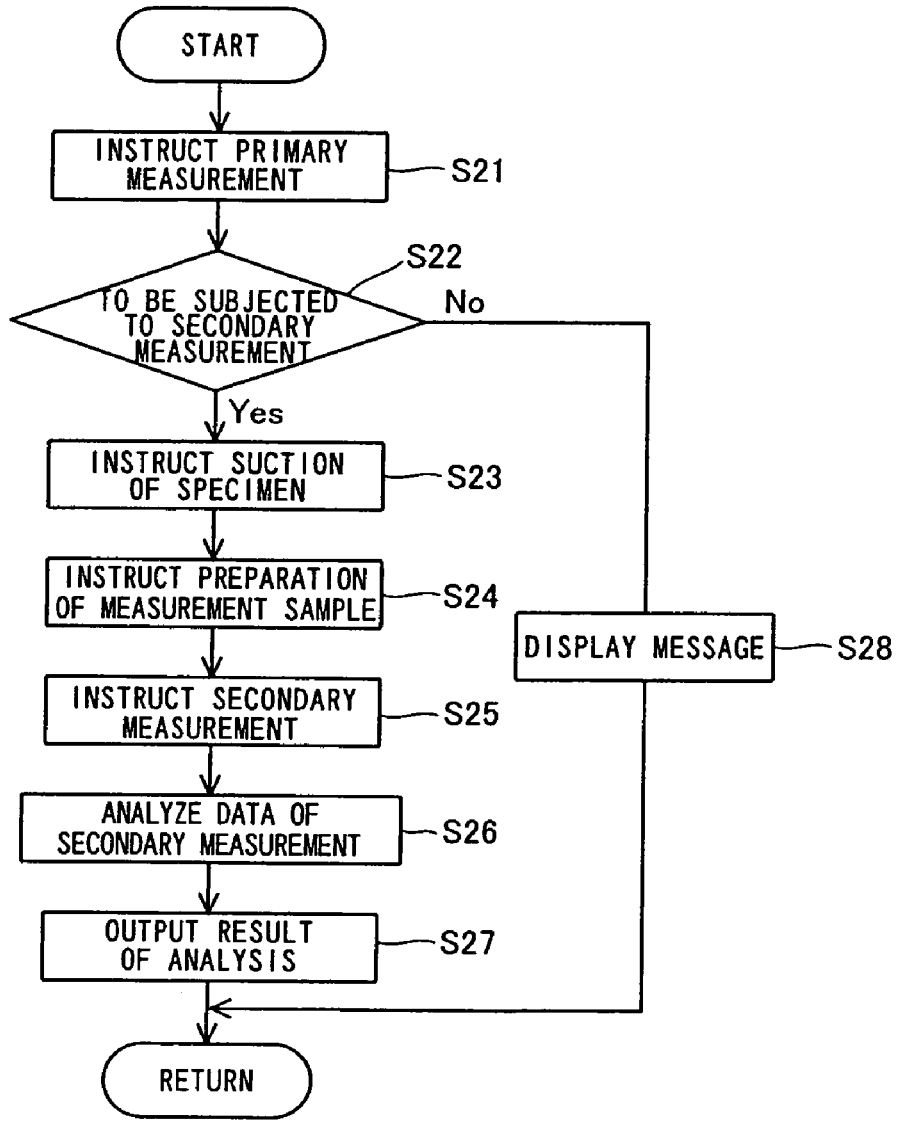
FIG. 16 is a flow chart showing the details (subroutine) of analysis with the PC body at a step S3 shown in FIG. 13.

At a step S26 in FIG. 16, the PC body 3b selects optical information (data) suitable for analysis from among 10 types of optical information (data) having different wavelength characteristics and different amplification rates received from the second optical information acquisitive portion 80, i.e., among data of the low and high gains corresponding to the five types of optical filters 14b to 14f respectively, on the basis of the results of analysis of the optical information (data) from the first optical information acquisitive portion 70 acquired at the step S22 and analyzes the optical information. At a step S27, the PC body 3b outputs the results of analysis of the measurement samples (coagulation curve and coagulation time shown in FIG. 18 in this embodiment) to the display portion 3c.

Data acquisition with the control portion 112 according to this embodiment is now described with reference to FIGS. 9, 13, 15, 17 and 19. The PC body 3b instructs analysis (step S3), in order to start this data acquisition.

Figure 19:
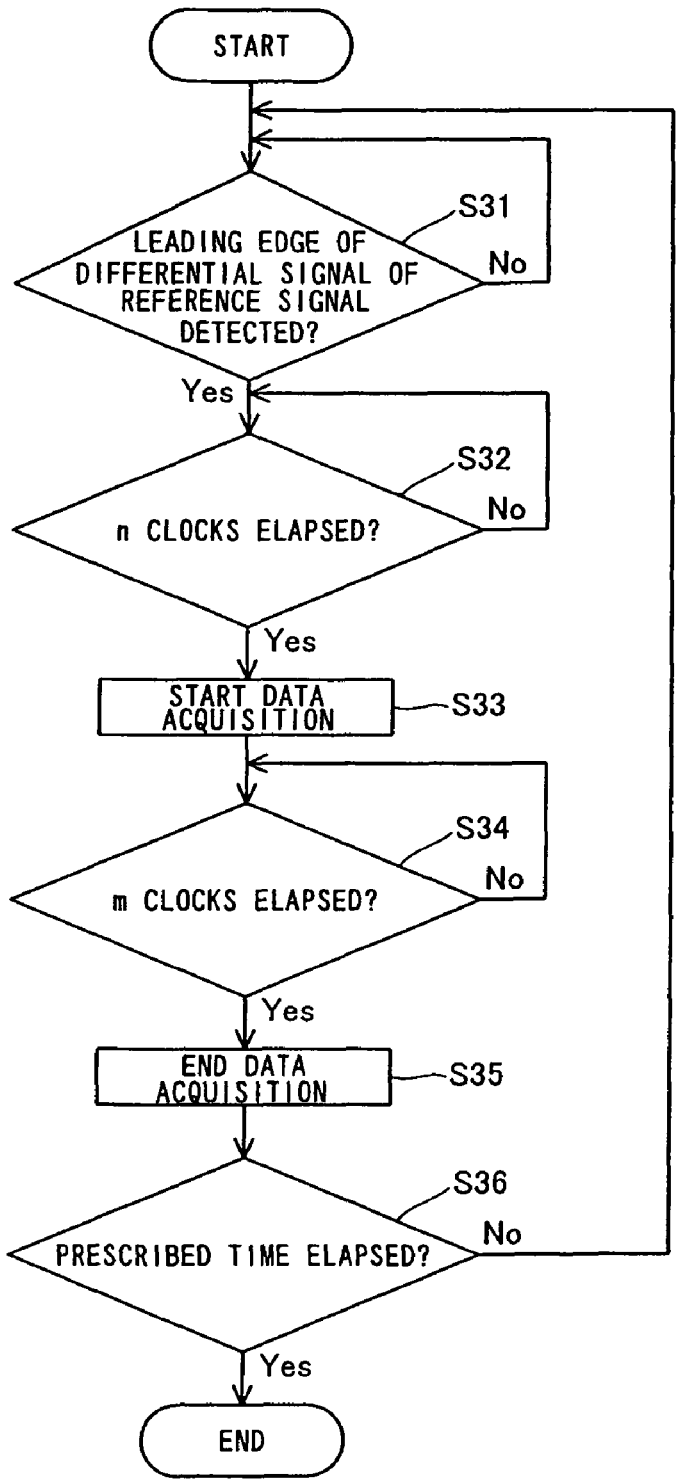
FIG. 19 is a flow chart for illustrating a method of data acquisition with the control portion of the analyzer according to the embodiment of the present invention.

At a step S31 shown in FIG. 19, the control portion 112 (FIG. 9) waits for detection of the leading edge of the differential signal of the reference signal corresponding to N1 in FIG. 15. When detecting the leading edge of the differential signal of the reference signal, the control portion 112 waits for a lapse of n clocks calculated in the initialization from the leading edge of the differential signal of the reference signal.

At a step S33, the control portion 112 starts acquiring digital data output from the three A-D conversion portions 111d respectively. At a step S34, the control portion 112 waits for a lapse of m clocks from the start of digital data acquisition. Upon the lapse of m clocks, the control portion 112 ends the digital data acquisition at a step S35. At a step S36, the control portion 112 determines whether or not a prescribed time has elapsed from the time receiving the instruction for analysis from the PC body 3b. The control portion 112 ends the data acquisition if the prescribed time has elapsed, while returning to the step S31 if the prescribed time has not yet elapsed.

Data acquisition with the PC body 3b according to this embodiment is now described with reference to FIGS. 1, 9, 11, 18 and 20. The PC body 3b starts this processing upon power supply to the information processing terminal 3a.

Figure 20:
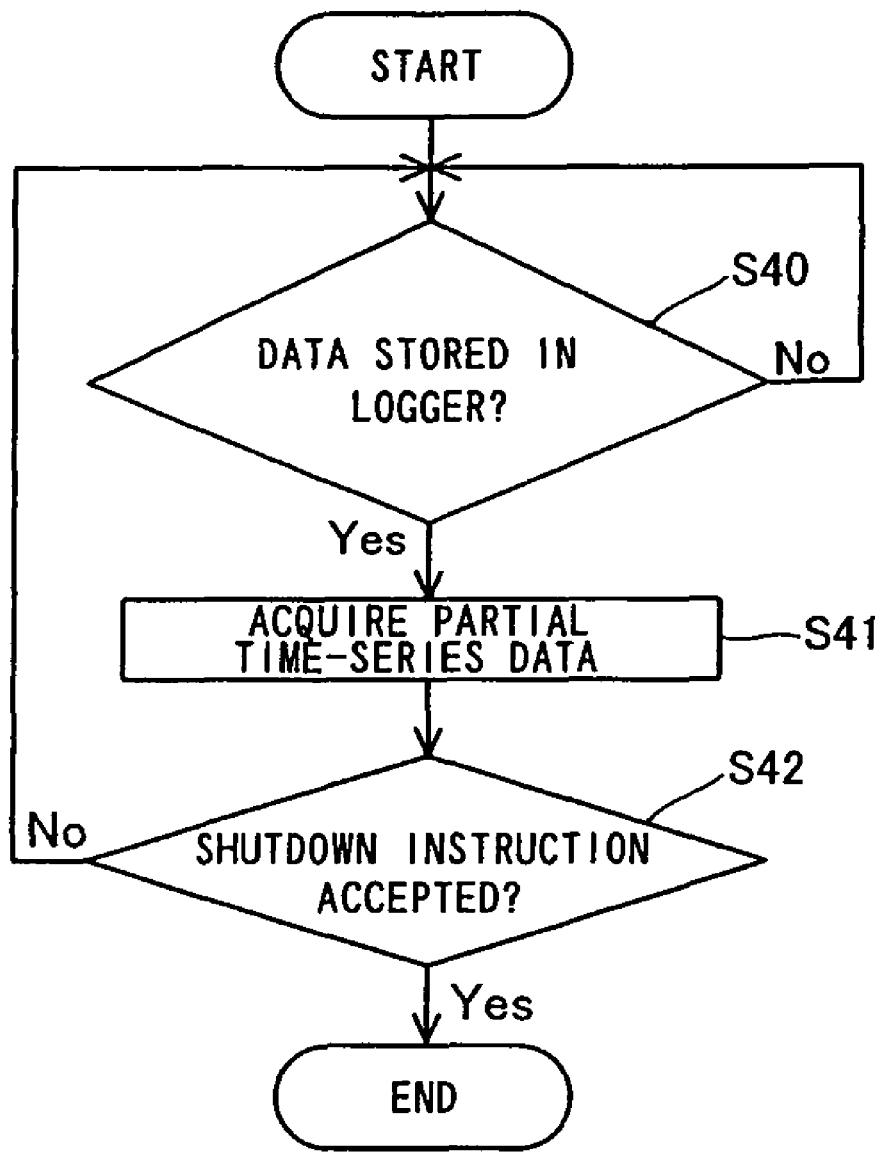
FIG. 20 is a flow chart for illustrating a method of data acquisition with the PC body of the analyzer according to the embodiment of the present invention.

At a step S40 in FIG. 20, the PC body 3b monitors whether or not the logger memory 112h has newly stored data, and waits until the logger memory 112h stores data for 100 msec. (corresponding to single rotation of the filter portion 14). More specifically, the PC body 3b waits for transmission of a notice from the control portion 112 indicating that the logger memory 112h has stored data for 100 msec. At a step S41, the PC body 3b acquires the data (partial time-series data) for 100 msec. through the interface 116 and the local bus interface 112k. In other words, the PC body 3b acquires data for 100 msec. corresponding to single rotation of the filter portion 14 stored in the areas 0 to 5 of the logger memory 112h as shown in FIG. 11.

At a step S42, the PC body 3b determines whether or not the information processing terminal 3a has accepted a shutdown instruction. When the information processing terminal 3a has accepted no shutdown instruction, the PC body 3b returns to the step S40. When the information processing terminal 3a has accepted the shutdown instruction, on the other hand, the PC body 3b ends the data acquisition. When carrying out the step S41 for the second time, the PC body 3b acquires data from the six areas 6 to 11 of the logger memory 112h subsequent to the areas 0 to 5, from which the data have been acquired at the first time. Thus, the PC body 3b successively acquires data from the logger memory 112h every six areas.

The PC body 3b creates prescribed time-series data by combining partial time-series data subsequent to the time when the cuvettes 152 (see FIG. 1) storing the measurement samples have been received in the receiving holes 81a of the second optical information acquisitive portion 80 among those acquired from the logger memory 112h at the step S41 in a time-series manner. Then, the PC body 3b creates the coagulation curve shown in FIG. 18 on the basis of the created time-series data, and obtains the coagulation times of the measurement samples from the created coagulation curve. More specifically, the PC body 3b obtains a time t when the intensity of the transmitted light components reaches 50%, i.e., the intermediate level between 100% and 0%, and calculates elapsed times from this time t as the coagulation times. The display portion 3c displays the coagulation times at the step S27 (see FIG. 16), as described above.

Monitoring on the rotation of the filter portion 14 is now described.

The control portion 112 parallelly and continuously executes the following three monitoring operations during the rotation of the filter portion 14. When causing an error in at least one of the three monitoring operations, the control portion 112 stops the filter portion 14 from rotating. The methods of the three monitoring operations on the rotation of the filter portion 14 are now described in detail.

A method of monitoring the time interval for detecting the origin slit 14k is described with reference to FIGS. 2, 3, 9, 21 and 22. According to this embodiment, the filter portion 14 of the lamp unit (see FIG. 3) continuously uninterruptedly rotates while a power source of the analyzer 3 (see FIG. 2) is in an ON-state. At this time, the filter rotation monitoring portion 112b of the control portion 112 (see FIG. 9) receives signals from the sensor 16 detecting the slits 14k and 14l of the rotating filter portion 14. When detecting the slits 14k and 14l, the sensor 16 outputs a signal rising to ON-states as shown in a waveform diagram of FIG. 22. At a step S51 shown in FIG. 21, the filter rotation monitoring portion 112b determines whether or not the sensor 16 has detected any slit on the basis of the signal received from the sensor 16. When detecting that the sensor 16 has detected no slit at the step S51, the filter rotation monitoring portion 112b repetitively determines whether or not the sensor 16 has detected passage of any slit at the step S51 again.

Figure 21:
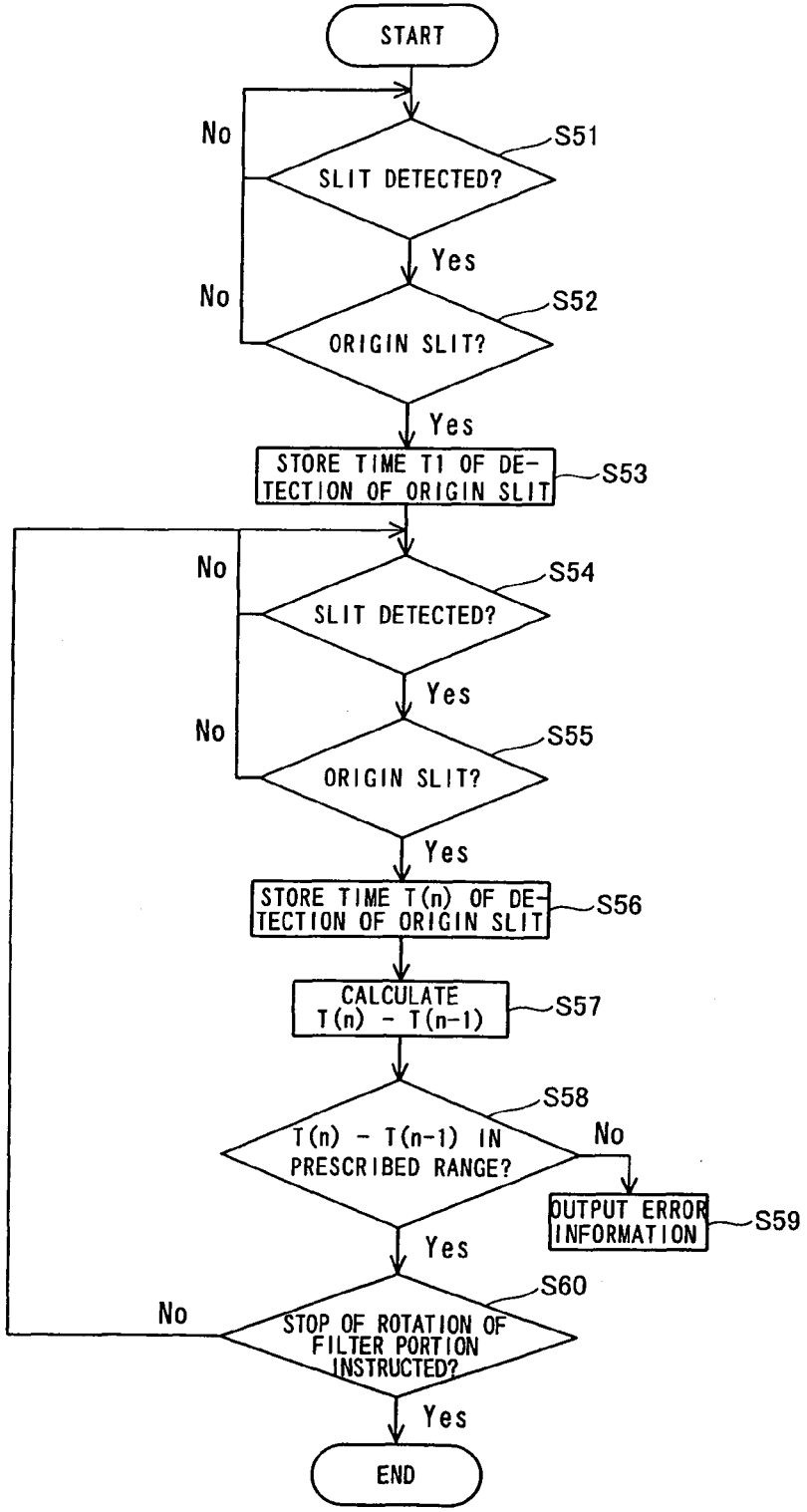
FIG. 21 is a flow chart showing processing of monitoring a time interval for detecting an origin slit in processing of monitoring rotation of the filter portion with the control portion of the analyzer according to the embodiment of the present invention.
Figure 22:
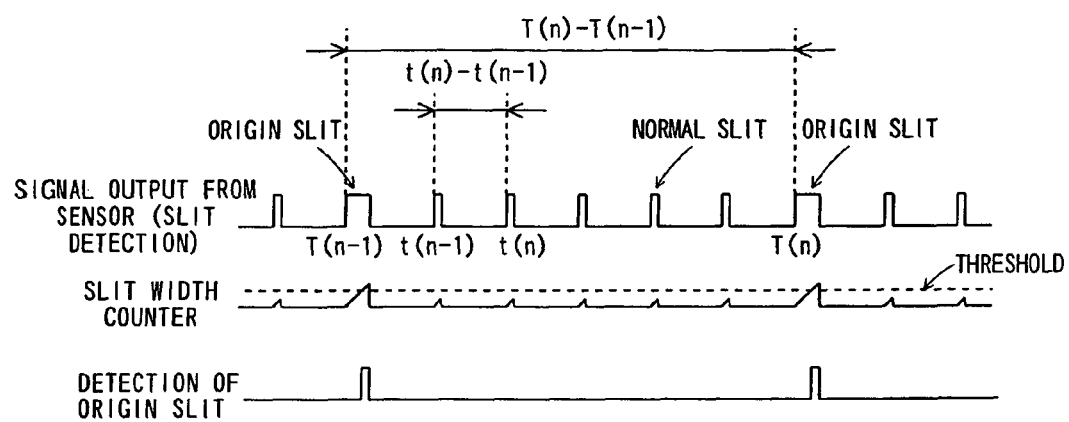
FIG. 22 is a waveform diagram showing the waveforms of a signal output from a sensor detecting slits of the rotating filter portion and an integral signal generated on the basis of the signal output from the sensor.

When determining that the sensor 16 has detected any slit at the step S51 shown in FIG. 21, on the other hand, the filter rotation monitoring portion 112b of the control portion 112 determines whether or not this slit is the origin slit 14k at a step S52. The filter rotation monitoring portion 112b makes this determination on the origin slit 14k on the basis of a signal generated by a slit width counter (not shown) provided therein. The slit width counter (not shown) generates an integral signal of the signal received from the sensor 16 as shown in FIG. 22. The ON-state period of the signal output from the sensor 16 upon detection of the origin slit 14k is longer than the ON-state period of the signal output from the sensor 16 upon detection of any normal slit 14l due to the width of the origin slit 14k larger than those of the remaining normal slits 14l. When the sensor 16 has detected the origin slit 14k, therefore, the integral signal generated by the slit width counter (not shown) of the filter rotation monitoring portion 112b rises up to a level higher than those of integral signals output upon detection of the normal slits 14*l*. Thus, the filter rotation monitoring portion 112*b* sets a prescribed threshold between the levels of rise of the integral signals output upon detection of the origin slit 14*k* and the normal slits 14*l*, for determining that the slit detected by the sensor 16 is the origin slit 14*k* when the corresponding integral signal reaches the prescribed threshold while determining that the slit detected by the sensor 16 is not the origin slit 14*k* (but any of the normal slits 14*l*) when the corresponding integral signal does not reach the prescribed threshold.

When determining that the slit detected by the sensor 16 is not the origin slit 14*k* at the step S52 in FIG. 21, the filter rotation monitoring portion 112*b* returns to the step S51. When determining that the slit detected by the sensor 16 is the origin slit 14*k*, on the other hand, the filter rotation monitoring portion 112*b* stores the time T1 when the sensor 16 has detected the origin slit 14*k* at a step S53. At a step S54, the filter rotation monitoring portion 112*b* determines whether or not the sensor 16 has detected another slit similarly to the aforementioned step S51. When determining that the sensor 16 has detected no slit at the step S54, the filter rotation monitoring portion 112*b* repetitively makes the determination at the step S54. When determining that the sensor 16 has detected another slit at the step S54, on the other hand, the filter rotation monitoring portion 112*b* determines whether or not the slit detected by the sensor 16 is the origin slit 14*k*, similarly to the aforementioned step S52.

When determining that the slit detected by the sensor 16 is not the origin slit 14*k*, the filter rotation monitoring portion 112*b* returns to the step S54. When determining that the slit detected by the sensor 16 is the origin slit 14*k* at the step S55, on the other hand, the filter rotation monitoring portion 112*b* stores the time T(n) when the sensor 16 has detected the origin slit 14*k* at a step S56. Referring to the time T(n), n represents the frequency of detection of the origin slit 14*k*. The sensor 16 has detected the origin slit 14*k* twice, and hence n=2 in this case.

At a step S57, the filter rotation monitoring portion 112*b* calculates T(n)−T(n−1), i.e., T2−T1 since n=2. In other words, the filter rotation monitoring portion 112*b* calculates the time interval between the first and second detection times T1 and T2 for the origin slit 14*k* at the step S57. At a step S58, the filter rotation monitoring portion 112*b* determines whether or not the time interval T2−T1 calculated at the step S57 is in the range of a prescribed time interval previously set as necessary for single rotation of the filter portion 14. When determining that the time interval T2−T1 is not in the range of the prescribed time interval at the step S58, the filter rotation monitoring portion 112*b* outputs error information indicating that the rotation of the filter portion 14 is abnormal to the controller status register 112*j* through the controller 112*a* at a step S59. At this time, the filter rotation monitoring portion 112*b* stops the filter portion 14 from rotating. The controller status register 112*j* temporarily stores the error information. Then, the controller status register 112*j* transmits the error information stored therein to the PC body 3*b* through the local bus interface 112*k* and the interface 116. Then, the PC body 3*b* displays an error message indicating that the rotation of the filter portion 14 is abnormal on the display portion 3*c* of the information processing terminal 3*a*.

When determining that the time interval T2−T1 is in the range of the prescribed time interval at the step S58, on the other hand, the filter rotation monitoring portion 112*b* determines whether or not the control portion 112 has instructed a stop of rotation of the filter portion 14 at a step S60. When determining that the control portion 112 has instructed no stop of rotation of the filter portion 14 at the step S60, the filter rotation monitoring portion 112*b* returns to the step S54. When determining that the control portion 112 has instructed a stop of rotation of the filter portion 14 at the step S60, on the other hand, the filter rotation monitoring portion 14 ends the monitoring operation on the rotation of the filter portion 14. The filter rotation monitoring portion 112*b* repeats the series of steps S54 to S60 until the same determines that the control portion 112 has instructed a stop of rotation of the filter portion 14 at the step S60.

An operation of monitoring the time interval for detecting two adjacent slits (the origin slit 14*k* and/or the normal slit(s) 14*l*) in the monitoring on the rotation of the filter portion 14 with the control portion 112 is now described with reference to FIGS. 2, 5, 9, 21 and 23.

Figure 23:
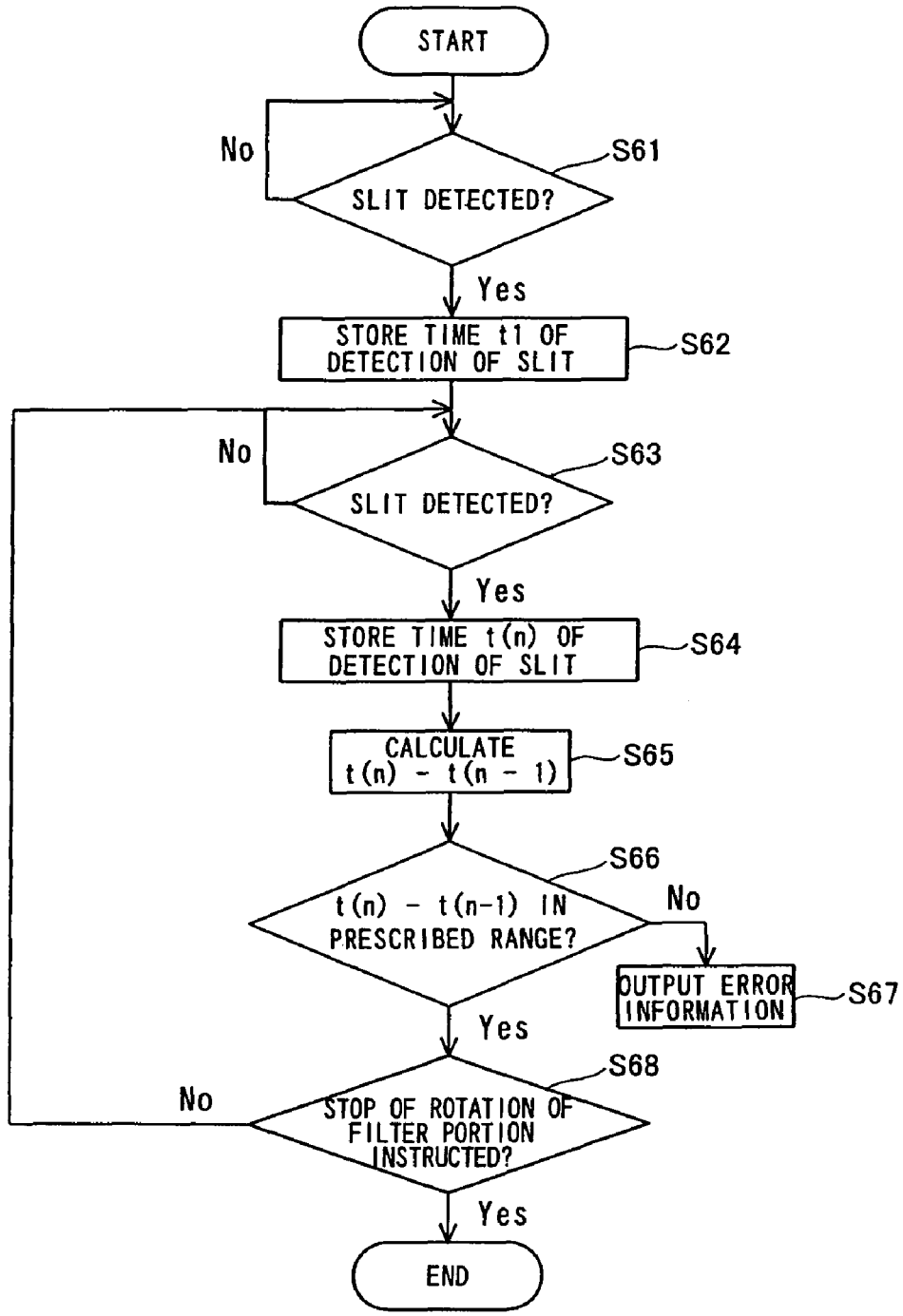
FIG. 23 is a flow chart showing processing of monitoring a time interval for detecting a pair of adjacent slits (the origin slit and/or normal slit(s)) in the processing of monitoring rotation of the filter portion with the control portion of the analyzer according to the embodiment of the present invention.

At a step S61 in FIG. 23, the filter rotation monitoring portion 112*b* of the control portion 112 (see FIG. 9) determines whether or not the sensor 16 has detected passage of any slit (the origin slit 14*k* (see FIG. 5) or any of the normal slits 14*l*) on the basis of the corresponding signal from the sensor 16, similarly to the step S51 shown in FIG. 21. When determining that the sensor 16 (see FIG. 9) has detected no slit at the step S61, the filter rotation monitoring portion 112*b* repeats the step S61. When determining that the sensor 16 has detected passage of any slit, on the other hand, the filter rotation monitoring portion 112*b* stores the time t1 when the sensor 16 has detected this slit at a step S62.

At a step S63, the filter rotation monitoring portion 112*b* determines whether or not the sensor 16 has detected passage of another slit, similarly to the aforementioned step S61. When determining that the sensor 16 has detected passage of no slit at the step S63, the filter rotation monitoring portion 112*b* repeats the step S63. When determining that the sensor 16 has detected passage of another slit at the step S63, on the other hand, the filter rotation monitoring portion 112*b* stores the time t(n) when the sensor 16 has detected this slit at a step S64. Referring to the time t(n), n represents the frequency of detection of slits by the sensor 16. The sensor 16 has detected the slits twice, and hence n=2 in this case.

At a step S65, the filter rotation monitoring portion 112*b* calculates t(n)−t(n−1), i.e., t2−t1 since n=2. In other words, the filter rotation monitoring portion 112*b* calculates the time interval between the first and second slit detection times t1 and t2 at the step S65. At a step S66, the filter rotation monitoring portion 112*b* determines whether or not the time interval t2−t1 calculated at the step S65 is in the range of a prescribed time interval previously set as that between the times for detecting two adjacent slits respectively. This time interval is either a first time interval required for normal passage of the optical filter 14*e* following passage of the optical filter 14*f* or a second time interval required for normal passage of the optical filter 14*f* following passage of the optical filter 14*b*.

When determining that the time interval t2−t1 is neither in the range of the aforementioned first time interval nor in the range of the aforementioned second time interval at the step S66, the filter rotation monitoring portion 112*b* outputs error information indicating that the rotation of the filter portion 14 is abnormal to the controller status register 112*j* through the controller 112*a* at a step S67. At this time, the filter rotation monitoring portion 112*b* stops the filter portion 14 from rotating. The controller status register 112*j* temporarily stores the error information. Then, the controller status register 112*j* transmits the error information stored therein to the PC body 3*b* through the local bus interface 112*k* and the interface 116. Then, the PC body 3*b* displays an error message indicating that the rotation of the filter portion 14 is abnormal on the display portion 3c of the information processing terminal 3a (see FIG. 2).

When determining that the time interval t2-t1 is in the range of the prescribed time interval at the step S66, on the other hand, the filter rotation monitoring portion 112b determines whether or not the control portion 112 has instructed a stop of rotation of the filter portion 14 at a step S68. When determining that the control portion 112 has instructed no stop of rotation of the filter portion 14 at the step S68, the filter rotation monitoring portion 112b returns to the step S63. When determining that the control portion 112 has instructed a stop of rotation of the filter portion 14 at the step S68, on the other hand, the filter rotation monitoring portion 112b ends the monitoring operation on the rotation of the filter portion 14. The filter rotation monitoring portion 112b repeats the series of steps S61 to S68 until the same determines that the control portion 112 has instructed a stop of rotation of the filter portion 14 at the step S68.

An operation of monitoring the number of the normal slits 14l detected while the origin slit 14k is detected twice in the monitoring on the rotation of the filter portion 14 with the control portion 112 according to this embodiment is described with reference to FIGS. 2, 5, 9, 21 and 24.

Figure 24:
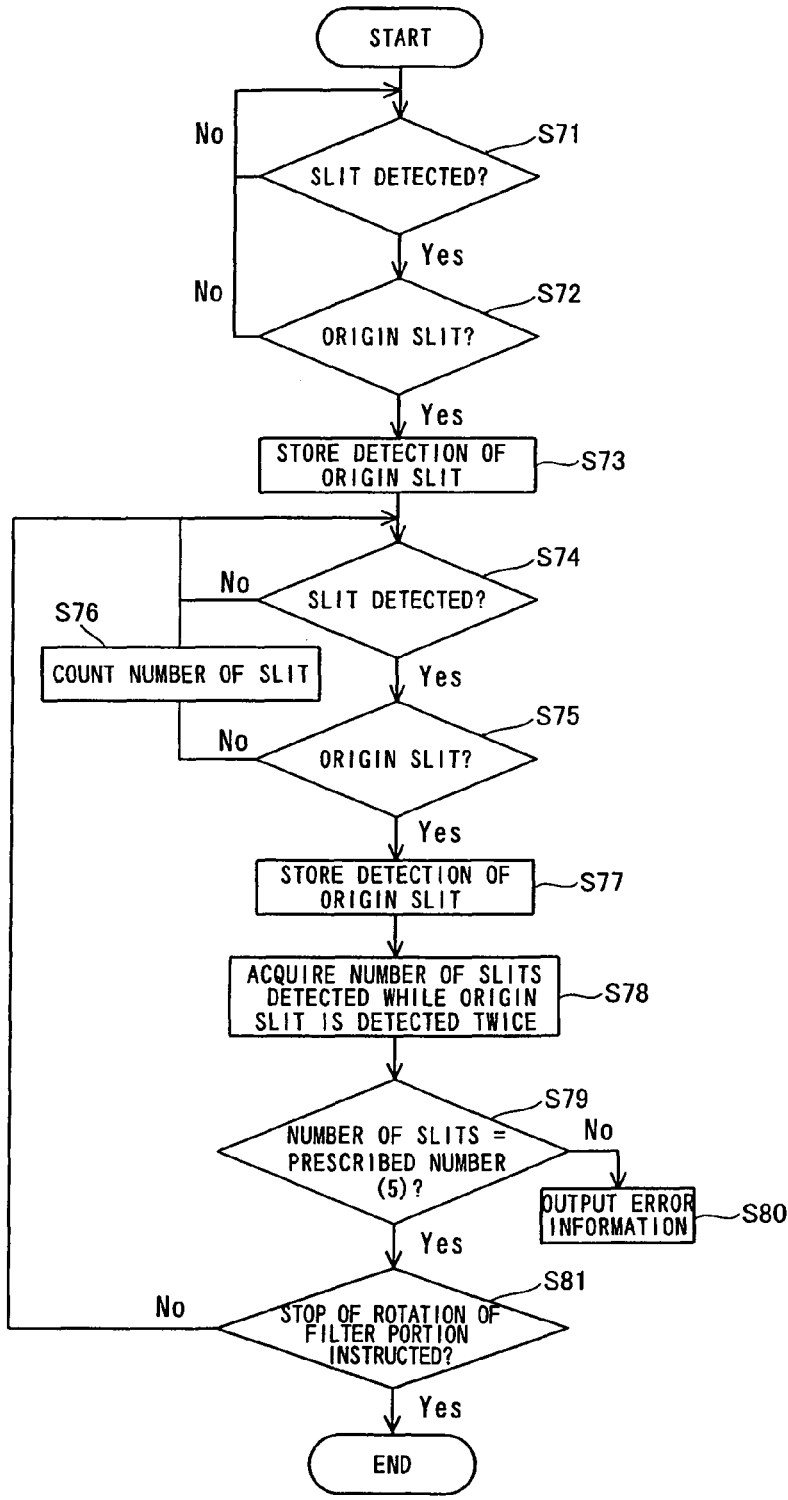
FIG. 24 is a flow chart showing processing of monitoring the number of normal slits detected while the origin slit is detected twice in the processing of monitoring rotation of the filter portion with the control portion of the analyzer according to the embodiment of the present invention.

At a step S71 shown in FIG. 24, the filter rotation monitoring portion 112b of the control portion 112 (see FIG. 9) determines whether or not the sensor 16 has detected any slit of the rotating filter portion 14 (see FIG. 15) on the basis of the corresponding signal from the sensor 16, similarly to the step S51 shown in FIG. 21. When determining that the sensor 16 (see FIG. 9) has detected no slit at the step S71, the filter rotation monitoring portion 112b repeats the step S71.

When determining that the sensor 16 has detected any slit at the step S71, on the other hand, the filter rotation monitoring portion 112b determines whether or not the slit detected by the sensor 16 is the origin slit 14k at a step S72, similarly to the step S52 shown in FIG. 21. When determining that the detected slit is not the origin slit 14k at the step S72, the filter rotation monitoring portion 112b returns to the step S71. When determining that the detected slit is the origin slit 14k at the step S72, on the other hand, the filter rotation monitoring portion 112b stores the information indicating that the sensor 16 has detected the origin slit 14k at a step S73.

At a step S74, the filter rotation monitoring portion 112b determines whether or not the sensor 16 has detected another slit, similarly to the aforementioned step S71. When determining that the sensor 16 has detected no slit at the step S74, the filter rotation monitoring portion 112b repeats the step S74. When determining that the sensor 16 has detected another slit at the step S74, on the other hand, the filter rotation monitoring portion 112b determines whether or not the detected slit is the origin slit 14k at a step S75, similarly to the aforementioned step S72. When determining that the detected slit is not the origin slit 14k (but any of the normal slits 14l) at the step S75, the filter rotation monitoring portion 112b counts the number of the slit (normal slit 14l) detected at the step S75 at a step S76. Thereafter the filter rotation monitoring portion 112b returns to the step S74.

When determining that the detected slit is the origin slit 14k at the step S75, on the other hand, the filter rotation monitoring portion 112b stores the information indicating that the sensor 16 has detected the origin slit 14k at a step S77. At a step S78, the filter rotation monitoring portion 112b acquires the number of the normal slits 14l counted at the step S76 as that of the normal slits 14l detected while the origin slit 14k has been detected twice. At a step S79, the filter rotation monitoring portion 112b determines whether or not the number of the normal slits 14l acquired at the step S78 is a prescribed number (5). When determining that the acquired number of the normal slits 14l is not the prescribed number (5) at the step S79, the filter rotation monitoring portion 112b outputs error information indicating that the rotation of the filter portion 14 is abnormal to the controller status register 112j through the controller 112a at a step S80. At this time, the filter rotation monitoring portion 112b stops the filter portion 14 from rotating. The controller status register 112j temporarily stores the error information. Then, the controller status register 112j transmits the error information stored therein to the PC body 3b through the local bus interface 112k and the interface 116. Then, the PC body 3b displays an error message indicating that the rotation of the filter portion 14 is abnormal on the display portion 3c of the information processing terminal 3a.

When determining that the acquired number of the normal slits 14l is the prescribed number (5) at the step S79, on the other hand, the filter rotation monitoring portion 112b determines whether or not the control portion 112 has instructed a stop of rotation of the filter portion 14 at a step S81. When determining that the control portion 112 has instructed no stop of rotation of the filter portion 14 at the step S81, the filter rotation monitoring portion 112b returns to the step S74. When determining that the control portion 112 has instructed a stop of rotation of the filter portion 14 at the step S81, on the other hand, the filter rotation monitoring portion 14 ends the monitoring operation on the rotation of the filter portion 14. The filter rotation monitoring portion 112b repeats the series of steps S74 to S81 until the same determines that the control portion 112 has instructed a stop of rotation of the filter portion 14 at the step S81.

According to this embodiment, as hereinabove described, the two optical fiber members 17b and 17a guide the light components emitted from the lamp unit 5 to the measurement samples provided on the analyzer 3 and the extension analyzer 4 respectively so that no individual lamp units may be provided for supplying light components to the measurement samples provided on the analyzer 3 and the extension analyzer 4 respectively, whereby the analytic system 1 can be downsized. Further, the analyzer 3 and the extension analyzer 4 are so separately provided that the analytic system 1 can parallelly treat various prescribed measurement samples (specimens) with the analyzer 3 and the extension analyzer 4. Thus, the analytic system 1 can improve specimen treatment efficiency in a case of acquiring optical information from a plurality of different measurement samples (specimens). Consequently, the analytic system 1 can improve specimen treatment efficiency while attaining downsizing.

According to this embodiment, the two optical fiber members 17a and 17b so branch the light components that the analytic system 1 can increase the quantities of light components emitted from exit end surfaces can be increased as compared with a case of branching light with a single optical fiber member.

According to this embodiment, the analytic system 1 guides the light components of the same characteristics emitted from the halogen lamp 11 to the measurement samples of the analyzer 3 and the extension analyzer 4 through the mirror 12b, the condensing lenses 13d to 13f and the optical fiber member 17b and through the mirror 12a, the condensing lenses 13a to 13c and the optical fiber member 17a respectively, whereby the analyzer 3 and the extension analyzer 4 can reduce the numbers of errors resulting from different characteristics of the light components applied to the measurement samples respectively.

According to this embodiment, the halogen lamp 11 of the lamp unit 5, formed by the platelike filament 11a capable of emitting light components from both surfaces thereof, can apply light components of substantially identical characteristics (quantities of light components etc.) from both surfaces of the platelike filament 11a, whereby the analytic system 1 can easily guide the light components of substantially identical characteristics emitted from both surfaces of the platelike filament 11a to the measurement samples of the analyzer 3 and the extension analyzer 4 through the mirror 12b, the condensing lenses 13d to 13f and the optical fiber member 17b and through the mirror 12a, the condensing lenses 13a to 13c and the optical fiber member 17a respectively.

Although the present invention has been described and illustrated in detail, it is clearly understood that the same is by way of illustration and example only and is not to be taken by way of limitation, the spirit and scope of the present invention being limited only by the terms of the appended claims.

For example, while the analytic system temporarily stores the data output from the detection portion and the signal processing portion in the logger memory of the control portion so that the PC body successively acquires the partial time-series data of the prescribed period from the data stored in the logger memory in the aforementioned embodiment, the present invention is not restricted to this but the analytic system may alternatively directly output the data from the detection portion or the signal processing portion to the PC body without temporarily storing the data in the logger memory.

While the control portion calculates the timing (n clocks) for starting signal acquisition on the basis of the differential signal of the reference signal and starts acquiring data upon a lapse of the calculated n clocks after the differential signal of the reference signal reaches the prescribed threshold in the aforementioned embodiment, the present invention is not restricted to this but the control portion may alternatively start data acquisition at previously set timing.

While the control portion starts data acquisition upon a lapse of n clocks from the leading edge of the differential signal of the reference signal corresponding to the reference light in the aforementioned embodiment, the present invention is not restricted to this but the control portion may alternatively start data acquisition upon a lapse of a prescribed period from the time when the sensor gas detected any slit.

While the present invention is applied to the analyzer performing coagulation measurement in the aforementioned embodiment, the present invention is not restricted to this but may also be applied to an analyzer (analytic system) performing measurement, other than coagulation measurement, requiring employment of a plurality of light components having different wavelength characteristics. For example, the present invention may be applied to a biochemical analyzer (analytic system).

While the information processing terminal is provided independently of the body of the analyzer in the aforementioned embodiment, the present invention is not restricted to this but the information processing terminal and the body of the analyzer may alternatively be integrated with each other.

While the analyzer is rendered extendable with the extension analyzer for treating a large number of specimens in the aforementioned embodiment, the present invention is not restricted to this but the analyzer may alternatively be rendered unextendable with any extension analyzer.

While the analytic system employs the multiplexers selecting the signals one by one from the plurality of analog signals output from the plurality of photoelectric conversion elements and successively outputting the same to the offset circuits in the aforementioned embodiment, the present invention is not restricted to this but the analytic system may alternatively employ an analog signal selector simultaneously selecting at least two signals from the plurality of analog signals output from the plurality of photoelectric conversion elements.

While the analytic system 1 bidirectionally emits light components from the filament 11a of the halogen lamp 11 for introducing the first light component into the optical fiber member 17a through the condensing lenses 13a to 13c while introducing the second light component into the optical fiber member 17b through the condensing lenses 13d to 13f in the aforementioned embodiment, the present invention is not restricted to this but the analytic system 1 may alternatively be provided with two halogen lamps (light sources) for introducing a light component emitted from the first halogen lamp into the optical fiber member 17a through the condensing lenses 13a to 13c while introducing a light component emitted from the second halogen lamp into the optical fiber member 17b through the condensing lenses 13d to 13f.

The invention claimed is:

1. A sample analyzer for optically analyzing samples, comprising:
    a first detection unit comprising a plurality of holders each of which is configured to receive a container that comprises a sample, and a plurality of light receiving elements corresponding to the plurality of holders;
    a second detection unit comprising a plurality of holders each of which is configured to receive a container that comprises a sample, and a plurality of light receiving elements corresponding to the plurality of holders;
    an optical source configured to emit light;
    an optical filter portion comprising a first optical filter which transmits a light of a first wavelength and a second optical filter which transmits a light of a second wavelength, wherein the optical filter portion rotates the first and second optical filters so as to be sequentially arranged on a first path of the light emitted from the optical source in a first direction and a second path of the light emitted from the optical source in a second direction different from the first direction;
    a first light guide portion which is arranged on the first path and is configured to receive the light emitted from the optical source through the first and the second optical filters, wherein the first light guide portion branches the received light into a plurality of light rays, and guides the branched plurality of light rays to the plurality of holders of the first detection unit respectively;
    a second light guide portion which is arranged on the second path and is configured to receive the light emitted from the optical source through the first and second optical filters wherein the second light guide portion branches the received light into a plurality of light rays, and guides the branched plurality of light rays to the plurality of holders of the second detection unit respectively; and
    an analytic portion configured to analyze a characteristic of a plurality of samples held by the plurality of holders of the first detection unit based on light detected by the receiving elements of the first detection unit, and to analyze a characteristic of a plurality of samples held by the plurality of holders of the second detection unit based on light detected by the receiving elements of the second detection unit.

2. The sample analyzer of claim 1, further comprising an injection portion configured to inject a reagent according to an analyzing item into containers held by the holders of the first and second detection units.

3. The sample analyzer of claim 1, wherein each of the first and second light guide portions comprises a plurality of optical fibers.

4. The sample analyzer of claim 3, wherein:
ends of the optical fibers of the first light guide portion and the light receiving elements of the first detection unit are opposed to each other through the holders of the first detection unit; and
ends of the optical fibers of the second light guide portion and the light receiving elements of the second detection unit are opposed to each other through the holders of the second detection unit.

5. The sample analyzer of claim 3, wherein:
each of the holders of the first and second detection units comprises a receiving hole for receiving a container that comprises a sample;
ends of the optical fibers of the first light guide portion and the light receiving elements of the first detection unit are opposed to each other through receiving holes of the holders of the first detection unit; and
ends of the optical fibers of the second light guide portion and the light receiving elements of the second detection unit are opposed to each other through receiving holes of the holders of the second detection unit.

6. The sample analyzer of claim 1, further comprising:
a first condensing portion configured to condense light emitted from the optical source in the first direction; and
a second condensing portion configured to condense light emitted from the optical source in the second direction, wherein:
light condensed by the first condensing portion is introduced into the first light guide portion; and
light condensed by the second condensing portion is introduced into the second light guide portion.

7. The sample analyzer of claim 1, further comprising:
a first reflecting member configured to change a traveling direction of light emitted from the optical source in the first direction and to introduce the reflected light into the first light guide portion; and
a second reflecting member configured to change a traveling direction of light emitted from the optical source in the second direction and to introduce the reflected light into the second light guide portion.

8. The sample analyzer of claim 7, wherein:
the optical source comprises a platelike filament configured for emitting light from a plurality of surfaces;
the first reflecting member is configured to change the traveling direction of light emitted from a first surface of the filament; and
the second reflecting member is configured to change the traveling direction of light emitted from a second surface of the filament.

9. The sample analyzer of claim 7, wherein each of the first and second light guide portions comprises a plurality of optical fibers.

10. The sample analyzer of claim 9, wherein:
ends of the optical fibers of the first light guide portion and the light receiving elements of the first detection unit are opposed to each other through the holders of the first detection unit; and
ends of the optical fibers of the second light guide portion and the light receiving elements of the second detection unit are opposed to each other through the holders of the second detection unit.

11. The sample analyzer of claim 1, wherein the samples comprise blood.

12. The sample analyzer of claim 1, wherein
the optical filter portion comprises a annular filter plate which is provided with the first and second optical filters: and
the first light guide portion and the second light guide portion are arranged symmetrically with respect to a central axis of the filter plate.

* * * * *

UNITED STATES PATENT AND TRADEMARK OFFICE
CERTIFICATE OF CORRECTION

| | | |
|---|---|---|
| PATENT NO. | : 7,916,298 B2 | Page 1 of 1 |
| APPLICATION NO. | : 12/655734 | |
| DATED | : March 29, 2011 | |
| INVENTOR(S) | : Norimasa Yamamoto | |

It is certified that error appears in the above-identified patent and that said Letters Patent is hereby corrected as shown below:

<u>In the Claims</u>

In column 28, claim 12, line 31, before "annular filter plate" replace "a" with --an--.

Signed and Sealed this
Twenty-fourth Day of April, 2012

David J. Kappos
*Director of the United States Patent and Trademark Office*